US012637491B2

(12) United States Patent
Van de Water et al.

(10) Patent No.: US 12,637,491 B2
(45) Date of Patent: May 26, 2026

(54) ANTIGENIC PEPTIDES AND USES THEREOF FOR DIAGNOSING AND TREATING AUTISM

(71) Applicant: The Regents of the University of California, Oakland, CA (US)

(72) Inventors: Judy Van de Water, Capay, CA (US); Elizabeth Edmiston, Sacramento, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 385 days.

(21) Appl. No.: 17/378,401

(22) Filed: Jul. 16, 2021

(65) Prior Publication Data

US 2021/0347824 A1     Nov. 11, 2021

Related U.S. Application Data

(60) Division of application No. 15/847,477, filed on Dec. 19, 2017, now Pat. No. 11,098,082, which is a continuation of application No. PCT/US2016/039029, filed on Jun. 23, 2016.

(60) Provisional application No. 62/185,186, filed on Jun. 26, 2015.

(51) Int. Cl.

| | |
|---|---|
| *C07K 7/08* | (2006.01) |
| *A61K 9/00* | (2006.01) |
| *A61P 25/00* | (2006.01) |
| *G01N 33/564* | (2006.01) |

(52) U.S. Cl.
CPC .............. *C07K 7/08* (2013.01); *A61K 9/0019* (2013.01); *A61P 25/00* (2018.01); *G01N 33/564* (2013.01); *G01N 2800/28* (2013.01); *G01N 2800/50* (2013.01)

(58) Field of Classification Search
CPC ......... C07K 7/08; A61K 9/0019; A61P 25/00; G01N 33/564; G01N 2800/28; G01N 33/6896; G01N 2800/50; Y02A 50/30
See application file for complete search history.

(56) References Cited

U.S. PATENT DOCUMENTS

| | | | |
|---|---|---|---|
| 4,833,092 | A | 5/1989 | Geysen |
| 7,452,678 | B2 | 11/2008 | Durham et al. |
| 7,452,681 | B2 | 11/2008 | Amaral et al. |
| 7,741,464 | B2 | 6/2010 | Terng et al. |
| 7,745,391 | B2 | 6/2010 | Mintz et al. |
| 8,043,820 | B2 | 10/2011 | Amaral et al. |
| 8,383,360 | B2 | 2/2013 | Van de Water et al. |
| 8,518,651 | B2 | 8/2013 | Sato et al. |
| 9,529,001 | B2 | 12/2016 | Van de Water et al. |
| 11,098,082 | B2 | 8/2021 | Van De Water |
| 2003/0064411 | A1 | 4/2003 | Herath |
| 2005/0106143 | A1 | 5/2005 | Giraudon |
| 2009/0074667 | A1 | 3/2009 | Amaral et al. |
| 2009/0286238 | A1 | 11/2009 | Craddock et al. |
| 2010/0075354 | A1 | 3/2010 | Sato et al. |
| 2011/0033875 | A1 | 2/2011 | Pierce et al. |
| 2011/0038872 | A1 | 2/2011 | Van de Water et al. |
| 2012/0196307 | A1 | 8/2012 | Ottens et al. |
| 2013/0210037 | A1 | 8/2013 | Van de Water et al. |
| 2014/0134187 | A1 | 5/2014 | Nath et al. |
| 2017/0191994 | A1 | 7/2017 | Van de Water et al. |

FOREIGN PATENT DOCUMENTS

| | | |
|---|---|---|
| CA | 2279834 A1 | 8/1998 |
| CA | 2391568 A1 | 12/2002 |
| CA | 2630796 A1 | 6/2007 |
| CA | 2649859 A1 | 5/2008 |
| CN | 101336372 A | 12/2008 |
| EP | 1983003 A2 | 10/2008 |
| JP | 2005-507242 A | 3/2005 |
| JP | 2007-512027 A | 5/2007 |
| JP | 2009-526541 A | 7/2009 |
| WO | 0246767 A2 | 6/2002 |
| WO | 02/101008 A2 | 12/2002 |

(Continued)

OTHER PUBLICATIONS

Mexico Patent Office, official action issued Nov. 11, 2021, related Mexico patent application No. MX/a/2017/016329, pp. 1-7, English-language translation, pp. 8-13, claims examined, pp. 14-16.
IP Australia, Examination report No. 1 issued Aug. 3, 2021, related Australian patent application No. 2016281649, pp. 1-5, claims examined, pp. 6-11.
Abcam catalog, 2004, product sheet, LDH Elisa kit, abs 116693.
Ashwood et al., "A review of autism and the immune response," Clinical and Developmental Immunology, vol. 11(2), pp. 165-174 (Jun. 2004).
Ashwood et al., "Is autism an autoimmune disease?" Autoimmune Rev., vol. 3(7-8), 13 pgs. (Nov. 2004).
Azad et al., "Comparative Detection of Measles Specific IGM Antibody in Serum and Saliva by an Antibody-Capture IGM Enzyme Immunoassay (EIA)," Iranian Journal of Allergy, Asthma and Immunology, 2003, vol. 2, No. 3, pp. 149-154.

(Continued)

*Primary Examiner* — Olga N Chernyshev
(74) *Attorney, Agent, or Firm* — MARSHALL, GERSTEIN & BORUN LLP

(57)     ABSTRACT

The present invention provides peptides that specifically bind to maternal autoantibodies that are generated in the mother or potential mother against one or more endogenous polypeptide antigens selected from lactate dehydrogenase A (LDH A), lactate dehydrogenase B (LDH B), stress-induced phosphoprotein 1 (STIP1), guanine deaminase (GDA), Y Box Binding Protein 1 (YBX1), collapsin response mediator protein 1 (CRMP1), and collapsin response mediator protein 2 (CRMP2). The peptides described herein are useful for determining a risk of an offspring for developing an autism spectrum disorder (ASD) by detecting the presence of maternal autoantibodies in a biological sample of the mother or potential mother. The peptides or mimotopes thereof can also be administered to the mother or potential mother to block the binding between maternal autoantibodies and their antigens, thereby neutralizing the maternal autoantibodies.

27 Claims, No Drawings

Specification includes a Sequence Listing.

(56)                References Cited

FOREIGN PATENT DOCUMENTS

WO        2004/060302 A2    7/2004
WO        2005/007090 A2    1/2005
WO        2005/081714 A2    9/2005
WO        2006/091734 A2    8/2006
WO         2006091743       8/2006
WO        2006/121912 A2    11/2006
WO        2006/121952 A2    11/2006
WO        2007/093807 A2    8/2007
WO        2008/021290 A2    2/2008
WO        2008/070311 A2    6/2008
WO        2008/099972 A1    8/2008
WO        2009/075883 A2    6/2009
WO        2011/019929 A1    2/2011
WO        2016/210137 A1    12/2016

OTHER PUBLICATIONS

Bauman et al., "The development of mother-infant interactions after neonatal amygdale lesions in rhesus monkeys," The Journal of Neuroscience, vol. 24(3), pp. 711-721 (Jan. 21, 2004).

Bauman et al., "The development of social behavior following neonatal amygdale lesions in rhesus monkeys," Journal of Cognitive Neuroscience, vol. 16(8), pp. 1388-1411 (2004).

Becker et al., "Autoantibodies to Lactate Dehydrogenase in Serum Identified by Use of Immobilized Protein G and Immobilized Jacalin, a Jackfruit Lectin," Clin. Chem., 1989, 35(1), pp. 2190-2195.

Braunschweig et al., "Autism: Maternally derived antibodies specific for fetal brain proteins," Neurotoxicology, Tox Press, vol. 9, No. 2, Nov. 2007, pp. 226-231.

Braunschweig, D. et al., "Autism-specific maternal autoantibodies recognize critical proteins in developing brain," Transl Psychiatry, 3:e277, 2013.

Cabanlit et al., "Brain-specific Autoantibodies in the Plasma of Subjects with Autistic Spectrum Disorder," Ann. N.Y. Acad. Sci., vol. 1107, pp. 92-103 (2007).

Chauhan et al., "Increased Oxidative Damage and Free Radical Generation in Lymphoblasts from Autism," J. Neurochem, 2008, 106(1), p. 44.

Chen, Ping, "Preparation of Recombinant Human Sperm-Specific Lactate Dehydrogenases Antigen and its Use in Detection of Autoantibodies for Infertility Investigation," Master's Thesis, Jul. 2007, 11 pages.

Connolly et al., "Serum autoantibodies to brain in Landau-Kleffner variant, autism, and other neurologic disorders," The Journal of Pediatrics, vol. 134(5), pp. 607-613 (May 1999).

Cook et al., "Receptor inhibition by immunoglobulins: Specific inhibition by autistic children, their relatives, and control subjects," Journal of Autism and Developmental Disorders, vol. 23(1), pp. 67-78 (1993).

Croen et al., "Maternal autoimmune diseases, asthma and allergies, and childhood autism spectrum disorders," Arch. Pediatr. Adolesc. Med., vol. 159, pp. 151-157 (Feb. 2005).

Dalton et al., "Maternal neuronal antibodies associated with autism and a language disorder," Annals of Neurology, vol. 53(4), pp. 533-537 (Apr. 2003).

Du et al., "Sequence Analysis, Cloning Expression and Immunogenicity Analysis of Lactate Dehydrogenase Gene from Taenia Solium," Conference proceedings of 6th Meeting and 10th Seminar for Chinese Association of Animal Science and Veterinary Medicine, Division of Domestic Animal and Parasitology, 101-110, 2009, China.

Eigsti et al., "A systems neuroscience approach to autism: Biological, cognitive and clinical perspectives," Mental Retardation and Developmental Disabilities, Research Reviews, vol. 9, pp. 206-216 (2003).

Emery et al., "The effects of bilateral lesions of the amygdala on dyadic social interactions in rhesus monkeys (Macaca mulatta)," Behavioral Neuroscience, vol. 115(3), pp. 515-544 (2001).

Flannery et al., "A test of the immunoreactive theory for the origin of neurodevelopmental disorders in the offspring of women with immune disorder," Cortex, vol. 30, pp. 635-646 (1994).

Gilling, M. et al., "A 3.2 Mb deletion on 18q12 in a patient with childhood autism and high-grade myopia," European Journal of Human Genetics, 16:312-19, 2008.

Gothard et al., "How do rhesus monkeys (Macaca mulatta) scan faces in a visual paired comparison task?" Anim. Cogn., vol. 7, pp. 25-36 (2004).

Kiessling et al., "Antineuronal antibodies: Tics and obsessive-compulsive symptoms," Developmental and Behavioral Pediatrics, vol. 15(6), pp. 421-425 (Dec. 1994).

Litt et al., "Detection of anti-pertussis toxin IgG in oral fluids for use in diagnosis and surveillance of Bordetella pertussis infection in children and young adults," Journal of Medical Microbiology, 2006, vol. 55, pp. 1223-1228.

Luzza et al., "Salivary Immunoglobulin G Assay to Diagnose Helicobacter pylori Infection in Children," Journal of Clinical Microbiology, 1997, vol. 35, No. 12, pp. 3358-3360.

Plioplys et al., "Anti-CNS antibodies in childhood neurologic diseases," Neuropediatrics, vol. 20, pp. 93-102 (1989).

Plioplys et al., "Lymphocyte function in autism and rett syndrome," Neuropsychobiology, vol. 29, pp. 12-16 (1994).

Prather et al., "Letter to Neuroscience: Increased social fear and decreased fear of objects in monkeys with neonatal amygdale lesions," Neuroscience, vol. 106(4), pp. 653-658 (2001).

Sankar, "Studies on blood platelets, blood enzymes, and leucocyte chromosome breakage in childhood schizophrenia," Behavioral Neuropsychiatry, vol. 2, No. 11, Feb. 1971, pp. 2-10.

Schorer, "Muscular dystrophy and the mind," Psychosomatic Medicine, vol. 26, Jan. 1964, pp. 5-13.

Shamy et al., Hippocampal volume is preserved and fails to predict recognition memory impairment in aged rhesus monkeys (Macaca mulatto), Neurobiology of Aging, 11 pgs. (2005).

Silva et al., "Autoantibody repertoires to brain tissue in autism nuclear families," Journal of Neuroimmunology, vol. 152, pp. 176-182 (2004).

Singer et al., "Antibodies against fetal brain in sera of mothers with autistic children," Journal of Neuroimmunology, vol. 194, No. 1-2, Feb. 2008, pp. 165-172.

Singer et al., "Prenatal exposure to antibodies from mothers of children with autism produces neurobehavioral alterations: a pregnant dam mouse model," Journal of Neuroimmunology, vol. 211, No. 1-2, Jun. 2009, pp. 39-48.

Singh et al., "Antibodies to myelin basic protein in children with autistic behavior," Brain, Behavior, and Immunity, vol. 7, pp. 97-103 (1993).

Singh et al., "Circulating autoantibodies to neuronal and glial filament proteins in autism," Pediatric Neurology, vol. 17(1), pp. 88-90 (1997).

Singh et al., "Immunodiagnosis and immunotherapy in autistic children," Ann. NY Acad. Sci., vol. 540, pp. 602-604 (1994).

Singh et al., "Prevalence of serum antibodies to caudate nucleus in autistic children," Neuroscience Letters, vol. 355, pp. 53-56 (2004).

Sparks et al., "Brain structural abnormalities in young children with autism spectrum disorder," Neurology, vol. 59, pp. 184-192 (Jul. 2002).

Thongcharoen et al., "Immunoglobulin G Antibody Capture Enzyme-Linked Immunosorbent Assay: a Versatile Assay for Detection of Anti-Human Immunodeficiency Virus Type 1 and 2 Antibodies in Body Fluids," Journal of Clinical Microbiology, 1992, vol. 30, No. 12, pp. 3288-3289.

Todd et al., "Demonstration of inter- and intraspecies differences in serotonin binding sites by antibodies from an autistic child," PNAS, vol. 82, pp. 612-616 (Jan. 1985).

Vargas et al., "Neuroglial activation and neuroinflammation in the brain of patients with autism," Ann. Neurol., vol. 57, pp. 67-81 (2005).

Warren et al., "Detection of maternal antibodies in infantile autism," J. Am. Acad. Child Adolesc. Psychiatry, vol. 29(6), pp. 873-877 (Nov. 1990).

(56)                    References Cited

OTHER PUBLICATIONS

Weizman et al., "Abnormal immune response to brain tissue antigen in the syndrome of autism," Am. J. Psychiatry, vol. 139(11), pp. 1462-1465 (Nov. 1982).
Willis et al., "Autoantibodies in Autism Spectrum Disorders (ASD)," Ann. N. Y. Acad. Sci. 1107, pp. 79-91 (2007).
Willis et al., "Detection of Autoantibodies to Neural Cells of the Cerebellum in the Plasma of Subjects with Autism Spectrum Disorders," Brain Behav Immun., vol. 23, No. 1, pp. 64-74 (2009).
PCT/US2016/039029, "Invitation to Pay Additional Fees," Sep. 30, 2016, 2 pages.
PCT/US2010/045343, "International Search Report," mailed Dec. 30, 2010, 6 pages.
European Application No. EP 16815305.4, "Partial Supplementary European Search Report", mailed Dec. 3, 2018, 15 pages.
European Application No. EP 16815305.4 , "Extended European Search Report", mailed Mar. 8, 2019, 13 pages.
IP Australia, Examination report No. 2 issued Apr. 26, 2022, related Australian patent application No. 2016281649, pp. 1-3, claims examined pp. 4-9.
Geysen, H. Mario, et al., "Use of peptide synthesis to probe viral antigens for epitopes to a resolution of a single amino acid", Proc. Natl. Acad. Sci., vol. 81, Jul. 1984, pp. 3998-4002.
Canadian Intellectual Property Office, second office action issued Aug. 3, 2023, related Canadian patent application No. 2,989,882, pp. 1-8, claims examined, pp. 9-12.
European Patent Office (EPO), Communication (Extended European Search Report) issued Feb. 20, 2024, related European patent application No. 23204324.0, pp. 1-10, with claims searched, 11-13.
Altschul et al., Basic local alignment search tool, J Mol Biol., 215(3):403-410 (Oct. 1990).
Altschul et al., Gapped BLAST and PSI-BLAST: a new generation of protein database search programs, Nucleic Acids Res., 25(17):3389-3402 (Sep. 1997).
Batzer et al., Enhanced evolutionary PCR using oligonucleotides with inosine at the 3'-terminus, Nucleic Acids Res., 19(18):5081 (Sep. 1991).
Burke et al., The Influence of Adjuvant on the Therapeutic Efficacy of a Recombinant Genital Herpes Vaccine, The Journal of Infectious Diseases, 170(5):1110-1119 (Nov. 1994).
Camarero et al., Biosynthesis of a Head-to-Tail Cyclized Protein with Improved Biological Activity, J. Am. Chem. Soc., 121(1):5597-5598 (1999).

Canadian Application No. 2989882, Office Action mailed Aug. 3, 2023.
Canadian Application No. 2989882, Office Action mailed Dec. 17, 2024.
Canadian Application No. 2989882, Office Action mailed Jun. 20, 2022.
International Application No. PCT/US2016/039029, International Preliminary Report on Patentability, mailed Jan. 4, 2018.
Kessel et al., Multimerization of Peptide Mimotopes for Blocking of Factor VIII Neutralizing Antibodies, Chem Med Chem., 4(8):1364-1370 (Aug. 2009).
Knittelfelder et al., Mimotope vaccination—from allergy to cancer, Expert Opin Biol Ther., 9(4):493-506 (Apr. 2009).
Millan et al., Epitopes of human testis-specific lactate dehydrogenase deduced from a cDNA sequence, PNAS U. S. A., 84(15):5311-5315 (Aug. 1987).
NCBI Reference Sequence: NM_001014809.1, *Homo sapiens* collapsin response mediator protein 1 (CRMP1), transcript variant 1, mRNA, GenBank (Dec. 14, 2013).
Ohtsuka et al., An alternative approach to deoxyoligonucleotides as hybridization probes by insertion of deoxyinosine at ambiguous codon positions, J. Biol. Chem., 260(5):2605-2608 (Mar. 1985).
Ozonoff et al., From Kanner to the millennium: Scientific advances that have shaped clinical practice, Autism spectrum disorders: A research review for practitioners, American Psychiatric Publishing, Inc., pp. 3-33 (2003).
Romanovskis et al., Preparation of head-to-tail cyclic peptides via side-chain attachment: Implications for library synthesis, The Journal of Peptide Research, 52(5):356-374 (Nov. 1998).
Rossolini et al., Use of deoxyinosine-containing primers vs degenerate primers for polymerase chain reaction based on ambiguous sequence information, Mol Cell Probes., 8(2):91-98 (Apr. 1994).
Sharav et al., Mimotope vaccines for cancer immunotherapy, Vaccine, 25(16):3032-3037 (Apr. 2007).
Tam et al., A biomimetic strategy in the synthesis and fragmentation of cyclic protein, Protein Science, 7(7):1583-1592 (Jul. 1998).
Tigges et al., Human herpes simplex virus (HSV)-specific CD8+ CTL clones recognize HSV-2-infected fibroblasts after treatment with IFN-gamma or when virion host shutoff functions are disabled, The Journal of immunology, 156 (10):3901-3910 (May 1996).
Valero et al., A comparative study of cyclization strategies applied to the synthesis of head-to-tail cyclic analogs of a viral epitope, The Journal of Peptide Research, 53(1):56-67 (Jan. 1999).
Yip et al., Epitope Discovery Using Monoclonal Antibodies and Phage Peptide Libraries, Combinatorial Chemistry High Throughput Screen, 2(3):125-128 (1999).

SEQUENCE LISTING

<160> NUMBER OF SEQ ID NOS: 121

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 1

Asp Leu Ala Asp Glu Leu Ala Leu Val Asp Val Ile Glu Asp Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 2

Ala Asp Glu Leu Ala Leu Val Asp Val Ile Glu Asp Lys Leu Lys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 3

Val Asp Val Ile Glu Asp Lys Leu Lys Gly Glu Met Met Asp Leu
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 4

Phe Leu Arg Thr Pro Lys Ile Val Ser Gly Lys Asp Tyr Asn Val
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 5

Met Lys Asn Leu Arg Arg Val His Pro Val Ser Thr Met Ile Lys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic -continued peptide epitope

<400> SEQUENCE: 6

Val His Pro Val Ser Thr Met Ile Lys Gly Leu Tyr Gly Ile Lys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 7

Cys His Gly Trp Val Leu Gly Glu His Gly Asp Ser Ser Val Pro
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 8

Leu Ile Ala Pro Val Ala Glu Glu Glu Ala Thr Val Pro Asn Asn
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 9

Pro Val Ala Glu Glu Glu Ala Thr Val Pro Asn Asn Lys Ile Thr
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 10

Leu Gln Thr Pro Lys Ile Val Ala Asp Lys Asp Tyr Ser Val Thr
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 11

Thr Pro Lys Ile Val Ala Asp Lys Asp Tyr Ser Val Thr Ala Asn
1               5                   10                  15

<210> SEQ ID NO 12

-continued

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 12

Asp Cys Ile Ile Ile Val Val Ser Asn Pro Val Asp Ile Leu Thr
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 13

Cys Ile Ile Ile Val Val Ser Asn Pro Val Asp Ile Leu Thr Tyr
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 14

Ile Ile Val Val Ser Asn Pro Val Asp Ile Leu Thr Tyr Val Thr
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 15

Val Ala Gly Val Ser Leu Gln Glu Leu Asn Pro Glu Met Gly Thr
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 16

Glu Ser Met Leu Lys Asn Leu Ser Arg Ile His Pro Val Ser Thr
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 17
```

Met Leu Lys Asn Leu Ser Arg Ile His Pro Val Ser Thr Met Val
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 18

Val Ser Thr Met Val Lys Gly Met Tyr Gly Ile Glu Asn Glu Val
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 19

Val Phe Leu Ser Leu Pro Cys Ile Leu Asn Ala Arg Gly Leu Thr
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 20

Val Leu Leu Gly Val Asp Leu Gly Ser Met Asp Glu Glu Glu Glu
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 21

Val Asp Leu Gly Ser Met Asp Glu Glu Glu Glu Ile Ala Thr Pro
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 22

Pro Pro Pro Pro Pro Pro Lys Lys Glu Thr Lys Pro Glu Pro Met
1               5                   10                  15

<210> SEQ ID NO 23
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide epitope

<400> SEQUENCE: 23

Thr Asn Gln Ala Ala Val Tyr Phe Glu Lys Gly Asp Tyr Asn Lys
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 24

Pro Pro Leu Ala His Ile Phe Arg Gly Thr Phe Val His Ser Thr
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 25

Ser Ser Ile Asp Leu Pro Leu Leu Glu Trp Leu Thr Lys Tyr Thr
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 26

Ala Thr Ile His Thr Asp Ser Ser Leu Leu Leu Ala Asp Ile Thr
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 27

Met Asp Leu Asn Asp Thr Phe Pro Glu Tyr Lys Glu Thr Thr Glu
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 28

Pro Ala Ala Pro Pro Ala Ala Pro Ala Leu Ser Ala Ala Asp Thr
1               5                   10                  15

-continued

```
<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 29

Ala Thr Lys Val Leu Gly Thr Val Lys Trp Phe Asn Val Arg Asn
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 30

Thr Val Lys Trp Phe Asn Val Arg Asn Gly Tyr Gly Phe Ile Asn
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 31

Phe Asn Val Arg Asn Gly Tyr Gly Phe Ile Asn Arg Asn Asp Thr
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 32

Glu Thr Val Glu Phe Asp Val Val Glu Gly Glu Lys Gly Ala Glu
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 33

Gly Ala Glu Ala Ala Asn Val Thr Gly Pro Gly Gly Val Pro Val
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 34
```

-continued

```
Arg Arg Pro Tyr Arg Arg Arg Arg Phe Pro Pro Tyr Tyr Met Arg
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 35

Pro Pro Arg Gln Arg Gln Pro Arg Glu Asp Gly Asn Glu Glu Asp
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 36

Val Val Pro Glu Pro Gly Ser Ser Leu Leu Thr Ser Phe Glu Lys
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 37

Thr Ser Phe Glu Lys Trp His Glu Ala Ala Asp Thr Lys Ser Cys
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 38

Val Asp Ile Thr Ser Trp Tyr Asp Gly Val Arg Glu Glu Leu Glu
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 39

Val Thr Ser Pro Pro Leu Ser Pro Asp Pro Thr Thr Pro Asp Tyr
1               5                   10                  15

<210> SEQ ID NO 40
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide epitope

<400> SEQUENCE: 40

Met Asp Glu Asn Gln Phe Val Ala Val Thr Ser Thr Asn Ala Ala
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 41

Val Gly Ser Asp Ala Asp Val Val Ile Trp Asp Pro Asp Lys Leu
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 42

Val Tyr Glu Val Pro Ala Thr Pro Lys Tyr Ala Thr Pro Ala Pro
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 43

Val Pro Ala Thr Pro Lys Tyr Ala Thr Pro Ala Pro Ser Ala Lys
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 44

Gln Ser Asn Phe Ser Leu Ser Gly Ala Gln Ile Asp Asp Asn Asn
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 45

Met Ala Glu Arg Lys Gln Ser Gly Lys Ala Ala Glu Asp Glu Glu
1               5                   10                  15
```

```
<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 46

Val Asn Asp Asp Gln Ser Phe Tyr Ala Asp Ile Tyr Met Glu Asp
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 47

Gly Glu Asn Leu Ile Val Pro Gly Gly Val Lys Thr Ile Glu Ala
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 48

Val Val Pro Glu Pro Gly Thr Ser Leu Leu Ala Ala Phe Asp Gln
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 49

Val Pro Glu Pro Gly Thr Ser Leu Leu Ala Ala Phe Asp Gln Trp
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 50

Gln Lys Ala Val Gly Lys Asp Asn Phe Thr Leu Ile Pro Glu Gly
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope
```

```
<400> SEQUENCE: 51

Thr Ser Pro Pro Leu Ser Pro Asp Pro Thr Thr Pro Asp Phe Leu
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 52

Val Gly Ser Asp Ala Asp Leu Val Ile Trp Asp Pro Asp Ser Val
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 53

Val Lys Thr Ile Ser Ala Lys Thr His Asn Ser Ser Leu Glu Tyr
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 54

Lys Thr Ile Ser Ala Lys Thr His Asn Ser Ser Leu Glu Tyr Asn
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 55

His Asn Ser Ser Leu Glu Tyr Asn Ile Phe Glu Gly Met Glu Cys
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 56

Glu Leu Arg Gly Val Pro Arg Gly Leu Tyr Asp Gly Pro Val Cys
1               5                   10                  15

<210> SEQ ID NO 57
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide epitope

<400> SEQUENCE: 57

Leu Arg Gly Val Pro Arg Gly Leu Tyr Asp Gly Pro Val Cys Glu
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 58

Arg Gly Val Pro Arg Gly Leu Tyr Asp Gly Pro Val Cys Glu Val
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 59

Gly Val Pro Arg Gly Leu Tyr Asp Gly Pro Val Cys Glu Val Ser
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 60

Val Pro Arg Gly Leu Tyr Asp Gly Pro Val Cys Glu Val Ser Val
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 61

Ser Leu Ser Gly Ala Gln Ile Asp Asp Asn Ile Pro Arg Arg Thr
1               5                   10                  15

<210> SEQ ID NO 62
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 62

Ala Asp Glu Leu Ala Leu Val Asp Val Ile Glu Asp Lys Leu Lys Gly
1               5                   10                  15
```

```
Glu Met Met Asp Leu
            20

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 63

Phe Leu Arg Thr Pro Lys Ile Val Ser Gly Lys Asp Tyr Asn Val
1               5                   10                  15

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 64

Met Lys Asn Leu Arg Arg Val His Pro Val Ser Thr Met Ile Lys Gly
1               5                   10                  15

Leu Tyr Gly Ile Lys
            20

<210> SEQ ID NO 65
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 65

Glu Lys Leu Ile Ala Pro Val Ala Glu Glu Glu Ala Thr Val Pro Asn
1               5                   10                  15

Asn Lys Ile Thr
            20

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 66

Ile Ala Pro Val Ala Glu Glu Glu Ala Thr Val Pro Asn Asn Lys Ile
1               5                   10                  15

Thr

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 67
```

-continued

```
Asp Cys Ile Ile Ile Val Val Ser Asn Pro Val Asp Ile Leu Thr Tyr
1               5                   10                  15

Val Thr

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 68

Val Ala Gly Val Ser Leu Gln Glu Leu Asn Pro Glu Met Gly Thr
1               5                   10                  15

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 69

Asn Glu Val Phe Leu Ser Leu Pro Cys Ile Leu Asn Ala Arg Gly Leu
1               5                   10                  15

Thr

<210> SEQ ID NO 70
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 70

Phe Leu Gln Thr Pro Lys Ile Val Ala Asp Lys Asp Tyr Ser Val Thr
1               5                   10                  15

Ala Asn

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 71

Leu Gln Thr Pro Lys Ile Val Ala Asp Lys Asp Tyr Ser Val Thr Ala
1               5                   10                  15

Asn

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 72

Glu Ser Met Leu Lys Asn Leu Ser Arg Ile His Pro Val Ser Thr Met
```

-continued

```
1               5               10              15

Val Lys Gly Met Tyr Gly Ile Glu Val
            20              25

<210> SEQ ID NO 73
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 73

Val Leu Leu Gly Val Asp Leu Gly Ser Met Asp Glu Glu Glu Glu Ile
1               5               10              15

Ala Thr

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 74

Pro Pro Pro Pro Pro Pro Pro Lys Lys Glu Thr Lys Pro Glu Pro Met
1               5               10              15

Glu

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 75

Pro Pro Pro Pro Pro Pro Lys Lys Glu Thr Lys Pro Glu Pro Met Glu
1               5               10              15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 76

Thr Asn Gln Ala Ala Val Tyr Phe Glu Lys Gly Asp Tyr Asn Lys
1               5               10              15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 77

Pro Pro Leu Ala His Ile Phe Arg Gly Thr Phe Val His Ser Thr
1               5               10              15
```

```
<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 78

Ser Ser Ile Asp Leu Pro Leu Leu Glu Trp Leu Thr Lys Tyr Thr
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 79

Ala Thr Ile His Thr Asp Ser Ser Leu Leu Leu Ala Asp Ile Thr
1               5                   10                  15

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 80

Ala Thr Lys Val Leu Gly Thr Val Lys Trp Phe Asn Val Arg Asn Gly
1               5                   10                  15

Tyr Gly Phe Ile Asn Arg Asn Asp Thr
            20                  25

<210> SEQ ID NO 81
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 81

Glu Thr Val Glu Phe Asp Val Val Glu Gly Glu Lys Gly Ala Glu Ala
1               5                   10                  15

Ala Asn Val Thr Gly Pro Gly Gly Val Pro Val
            20                  25

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 82

Arg Arg Pro Tyr Arg Arg Arg Arg Phe Pro Pro Tyr Tyr Met Arg
1               5                   10                  15

<210> SEQ ID NO 83
<211> LENGTH: 15
```

<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 83

Pro Pro Arg Gln Arg Gln Pro Arg Glu Asp Gly Asn Glu Glu Asp
1               5                   10                  15

<210> SEQ ID NO 84
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 84

Ser Phe Glu Lys Trp His Glu Ala Ala Asp Thr Lys Ser Cys
1               5                   10

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 85

Met Asp Glu Asn Gln Phe Val Ala Val Thr Ser Thr Asn Ala Ala
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 86

Val Pro Ala Thr Pro Lys Tyr Ala Thr Pro Ala Pro Ser Ala Lys
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 87

Val Thr Ser Pro Pro Leu Ser Pro Asp Pro Thr Thr Pro Asp Tyr Leu
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 88

Gln Ser Asn Phe Ser Leu Ser Gly Ala Gln Ile Asp Asp Asn Asn

-continued

```
1               5                    10                   15
```

```
<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 89

Val Asn Asp Asp Gln Ser Phe Tyr Ala Asp Ile Tyr Met Glu Asp
1               5                    10                   15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 90

Gly Glu Asn Leu Ile Val Pro Gly Gly Val Lys Thr Ile Glu Ala
1               5                    10                   15

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 91

Gln Lys Ala Val Gly Lys Asp Asn Phe Thr Leu Ile Pro Glu Gly
1               5                    10                   15

<210> SEQ ID NO 92
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 92

Val Lys Thr Ile Ser Ala Lys Thr His Asn Ser Ser Leu Glu Tyr Asn
1               5                    10                   15

Ile Phe Glu Gly Met Glu Cys
            20

<210> SEQ ID NO 93
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 93

Glu Leu Arg Gly Val Pro Arg Gly Leu Tyr Asp Gly Pro Val Cys Glu
1               5                    10                   15

Val Ser Val

<210> SEQ ID NO 94
```

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 94

Val Val Pro Glu Pro Gly Thr Ser Leu Leu Ala Ala Phe Asp Gln Trp
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 95

Thr Ser Pro Pro Leu Ser Pro Asp Pro Thr Thr Pro Asp Phe Leu
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 96

Ser Leu Ser Gly Ala Gln Ile Asp Asp Asn Ile Pro Arg Arg Thr
1               5                   10                  15

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Val Asp Val Ile Glu Asp Lys
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Val His Pro Val Ser Thr Met Ile Lys
1               5

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 99
```

```
Pro Val Ala Glu Glu Glu Ala Thr Val Pro Asn Asn
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 100

Ile Ile Val Val Ser Asn Pro Val Asp Ile Leu Thr
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 101

Thr Pro Lys Ile Val Ala Asp Lys Asp Tyr Ser Val Thr
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 102

Met Leu Lys Asn Leu Ser Arg Ile His Pro Val Ser Thr
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 103

Val Asp Leu Gly Ser Met Asp Glu Glu Glu Glu
1               5                   10

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 104

Pro Pro Pro Pro Pro Lys Lys Glu Thr Lys Pro Glu Pro Met Glu
1               5                   10                  15

<210> SEQ ID NO 105
<211> LENGTH: 9
<212> TYPE: PRT
<213> ORGANISM: Artificial Sequence
<220> FEATURE:
```

<223> OTHER INFORMATION: Description of Artificial Sequence: Synthetic
      peptide epitope

<400> SEQUENCE: 105

Thr Val Lys Trp Phe Asn Val Arg Asn
1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 106

Phe Asn Val Arg Asn
1               5

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 107

Phe Asn Val Arg Asn Gly Tyr Gly Phe Ile Asn
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 108

Val Pro Ala Thr Pro Lys Tyr Ala Thr Pro Ala Pro
1               5                   10

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 109

Thr Ser Phe Glu Lys
1               5

<210> SEQ ID NO 110
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 110

Val Pro Glu Pro Gly Thr Ser Leu Leu Ala Ala Phe Asp Gln
1               5                   10

<210> SEQ ID NO 111
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 111

Lys Thr Ile Ser Ala Lys Thr His Asn Ser Ser Leu Glu Tyr
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 112

His Asn Ser Leu Leu Glu Tyr
1               5

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 113

Arg Gly Val Pro Arg Gly Leu Tyr Asp Gly Pro Val Cys
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 114

Val Pro Arg Gly Leu Tyr Asp Gly Pro Val Cys
1               5                   10

<210> SEQ ID NO 115
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 115

Val Pro Arg Gly Leu Tyr Asp Gly Pro Val Cys Glu Val Ser
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 116

Asp Tyr Lys Asp Asp Asp Asp Lys Gly Gly
1               5               10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 117

Tyr Pro Tyr Asp Val Pro Asp Tyr Ala Gly
1               5               10

<210> SEQ ID NO 118
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide epitope

<400> SEQUENCE: 118

Lys Glu Val Pro Ala Leu Thr Ala Val Glu Thr Gly Ala Thr
1               5               10

<210> SEQ ID NO 119
<211> LENGTH: 12
<212> TYPE: DNA
<213> ORGANISM: Unknown
<220> FEATURE:
<223> OTHER INFORMATION: Description of Unknown:
      Y-box sequence

<400> SEQUENCE: 119
ctgattggcc aa                                               12

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Ser Gly Ser Gly Ser Gly
1               5

<210> SEQ ID NO 121
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Gly Ser Ser
1

95

ANTIGENIC PEPTIDES AND USES THEREOF FOR DIAGNOSING AND TREATING AUTISM

CROSS-REFERENCE TO RELATED APPLICATIONS

The present application is a divisional of U.S. application Ser. No. 15/847,477, filed Dec. 19, 2017, which is a continuation of International Patent Application No. PCT/US2016/039029, filed Jun. 23, 2016, which claims the benefit of and priority to U.S. Provisional Application No. 62/185,186, filed Jun. 26, 2015, the disclosures of which are herein incorporated by reference in their entirety for all purposes.

STATEMENT AS TO RIGHTS TO INVENTIONS MADE UNDER FEDERALLY SPONSORED RESEARCH OR DEVELOPMENT

This invention was made with Government support under Grant No. ES011269, awarded by the National Institutes of Health. The government has certain rights in this invention.

REFERENCE TO A "SEQUENCE LISTING"

The Sequence Listing written in file SequenceListing_070772-218220US-1253566.txt created on Jul. 14, 2021, 34,453 bytes, machine format IBM-PC, MS-Windows operating system, in accordance with 37 C.F.R. §§ 1.821-1.825, is hereby incorporated by reference in its entirety for all purposes.

BACKGROUND OF THE INVENTION

Autism spectrum disorders (ASD) are a set of neurodevelopmental disorders diagnosed in early childhood and are classified by a loss of abilities in social interaction, social communication, and the presence of repetitive and restricted interests and behaviors. Currently, ASD affects about 1 in 68 children in the United States (US), with an estimated cost to society at a staggering $240 billion per year. Current therapeutic interventions available for ASD are behaviorally directed or symptom-based pharmacological treatments applied only after diagnosis. Little is known about the cause of ASD and while certain therapeutic approaches applied following early diagnosis have shown promise, no preventive alternatives exist currently.

What is known is that activation of the maternal immune system during early fetal growth can have a negative effect on brain development. For reasons that are not clear, the immune system in some pregnant women produces autoantibodies (proteins produced by the immune system in response to a constituent of one's own tissues) that mistakenly identify parts of the fetal brain as foreign substances. As a result, gestational exposure to these maternal autoantibodies could lead to alterations in neurodevelopment characteristic of ASD. Indeed, 23% of mothers who gave birth to children with ASD have circulating autoantibodies against seven proteins highly expressed in the developing brain, in contrast to only 1% of mothers that deliver otherwise normal children. Each of the proteins is known to play an important role in neurodevelopment; interference with the level or function of more than one of them could act synergistically to change the trajectory of brain development. See, U.S. Pat. No. 8,383,360.

At present, there is no early, non-genetic, epitope-specific biomarker to determine the maternal risk of having a child with ASD. There is also a compelling need to address the cause and treatment of ASD, and not just the associated symptoms, by creating highly specific therapeutics and/or intervention tools. Early identification of these maternal autoantibodies in the affected mother would allow for early medical interventions to limit fetal exposure to autoantibodies and the consequent risk of her child developing ASD, thereby reducing the prevalence of ASD and improving the quality of life for otherwise affected children and their families. The present invention satisfies these needs and provides related advantages as well.

SUMMARY OF THE INVENTION

The present invention provides peptides (e.g., peptide epitopes) that specifically bind to maternal autoantibodies that are generated in the mother or potential mother against one or more polypeptides selected from lactate dehydrogenase A (LDH A), lactate dehydrogenase B (LDH B), stress-induced phosphoprotein 1 (STIP1), guanine deaminase (GDA), Y Box Binding Protein 1 (YBX1), collapsin response mediator protein 1 (CRMP1), and collapsin response mediator protein 2 (CRMP2). The peptides described herein are useful for determining a risk of an offspring for developing an autism spectrum disorder (ASD) by detecting the presence of maternal autoantibodies in a biological sample of the mother or potential mother. The peptides can also be administered to the mother or potential mother to block the binding between maternal autoantibodies and their antigens, thereby neutralizing the maternal autoantibodies. Furthermore, the peptides can be utilized in immunoadsorption to remove circulating autoantibodies from maternal plasma.

In a first aspect, provided herein is an isolated peptide having at least about 80% sequence identity to any one of SEQ ID NOS:1-7 and 62-64. In some embodiments, the peptide comprises at least 5, 6, 7, 8, 9, 10, 11, 12, 13, 14, or 15 contiguous amino acids of any one of SEQ ID NOS:1-7 and 62-64. In other embodiments, the peptide binds to a maternal antibody that binds to a lactate dehydrogenase A (LDH A) protein.

In a second aspect, provided herein is an isolated peptide having at least about 80% sequence identity to any one of SEQ ID NOS:8-19 and 65-72. In some embodiments, the peptide comprises at least 5, 6, 7, 8, 9, 10, 11, 12, 13, 14, or 15 contiguous amino acids of any one of SEQ ID NOS:8-19 and 65-72. In other embodiments, the peptide binds to a maternal antibody that binds to a lactate dehydrogenase B (LDH B) protein.

In a third aspect, provided herein is an isolated peptide having at least about 80% sequence identity to any one of SEQ ID NOS:20-23 and 73-76. In some embodiments, the peptide comprises at least 5, 6, 7, 8, 9, 10, 11, 12, 13, 14, or 15 contiguous amino acids of any one of SEQ ID NOS:20-23 and 73-76. In other embodiments, the peptide binds to a maternal antibody that binds to a stress-induced phosphoprotein 1 (STIP1) protein.

In a fourth aspect, provided herein is an isolated peptide having at least about 80% sequence identity to any one of SEQ ID NOS:24-27 and 77-79. In some embodiments, the peptide comprises at least 5, 6, 7, 8, 9, 10, 11, 12, 13, 14, or 15 contiguous amino acids of any one of SEQ ID NOS:24-27 and 77-79. In other embodiments, the peptide binds to a maternal antibody that binds to a guanine deaminase (GDA) protein.

In a fifth aspect, provided herein is an isolated peptide having at least about 80% sequence identity to any one of SEQ ID NOS:28-35 and 80-83. In some embodiments, the peptide comprises at least 5, 6, 7, 8, 9, 10, 11, 12, 13, 14, or 15 contiguous amino acids of any one of SEQ ID NOS:28-35 and 80-83. In other embodiments, the peptide binds to a maternal antibody that binds to a Y box binding protein 1 (YBX1) protein.

In a sixth aspect, provided herein is an isolated peptide having at least about 80% sequence identity to any one of SEQ ID NOS:36-44 and 84-88. In some embodiments, the peptide comprises at least 5, 6, 7, 8, 9, 10, 11, 12, 13, 14, or 15 contiguous amino acids of any one of SEQ ID NOS:36-44 and 84-88. In other embodiments, the peptide binds to a maternal antibody that binds to a collapsin response mediator protein 1 (CRMP1) protein.

In a seventh aspect, provided herein is an isolated peptide having at least about 80% sequence identity to any one of SEQ ID NOS:45-61 and 89-96. In some embodiments, the peptide comprises at least 5, 6, 7, 8, 9, 10, 11, 12, 13, 14, or 15 contiguous amino acids of any one of SEQ ID NOS:45-61 and 89-96. In other embodiments, the peptide binds to a maternal antibody that binds to a collapsin response mediator protein 2 (CRMP2) protein.

In certain embodiments, the peptide is from about 5 to 45 amino acids in length. In certain other embodiments, the peptide is from about 15 to about 30 amino acids in length. In other embodiments, the peptide is up to about 25 amino acids in length.

In particular embodiments, the peptide comprises an amino acid sequence consisting of any one of SEQ ID NOS:1-96.

In some embodiments, the peptide is a mimotope. In certain embodiments, the mimotope comprises D-amino acids. In some instances, all of the amino acids in the mimotope are D-amino acids. In other embodiments, the mimotope comprises one or more amino acid modifications (e.g., substitutions) relative to any one of SEQ ID NOS:1-96.

In some embodiments, any of the peptides described herein can further comprise a label such as a detectable label. In certain instances, the label is selected from the group consisting of biotin, a fluorescent label, a chemiluminescent label, and a radioactive label. In certain other instances, the label is attached (e.g., covalently attached) to the peptide.

In another aspect, provided herein is a composition including any one of the peptides described herein or a plurality thereof.

In some embodiments, the composition can further comprise a pharmaceutically acceptable carrier. In other embodiments, the plurality of peptides in the composition comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 different peptides, e.g., selected from SEQ ID NOS:1-96 and mimotopes thereof. In certain instances, the peptides in the composition may be derived from the same antigen and bind to the same maternal antibodies. In other instances, the peptides in the composition may be derived from different antigens and bind to different maternal antibodies. In yet other instances, the peptides in the composition may comprise a combination of peptides that bind to the same maternal antibodies and peptides that bind to one or more additional maternal antibodies. In some cases, each of the different peptides in the composition binds to the same maternal antibodies, e.g., all of the different peptides bind to maternal antibodies against a single antigen selected from LDH A, LDH B, STIP1, GDA, YBX1, CRMP1, and CRMP2. In other cases, each of the different peptides in the composition binds to at least 2, 3, 4, 5, 6, or 7 different maternal antibodies, e.g., the different peptides bind to maternal antibodies against 2, 3, 4, 5, 6, or all 7 of the following antigens: LDH A, LDH B, STIP1, GDA, YBX1, CRMP1, and CRMP2.

In yet another aspect, provided herein is a kit including any one of the peptides described herein or a plurality thereof and a solid support.

In some embodiments, the peptide of plurality of peptides can be immobilized on (e.g., covalently attached to) the solid support. In other embodiments, the solid support is a multiwell plate, an ELISA plate, a microarray, a chip, a bead, a porous strip, or a nitrocellulose filter.

In some embodiments, the plurality of peptides in the kit comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 different peptides, e.g., selected from SEQ ID NOS: 1-96 and mimotopes thereof. In certain instances, the peptides in the kit may be derived from the same antigen and bind to the same maternal antibodies. In other instances, the peptides in the kit may be derived from different antigens and bind to different maternal antibodies. In yet other instances, the peptides in the kit may comprise a combination of peptides that bind to the same maternal antibodies and peptides that bind to one or more additional maternal antibodies. In some cases, each of the different peptides in the kit binds to the same maternal antibodies, e.g., all of the different peptides bind to maternal antibodies against a single antigen selected from LDH A, LDH B, STIP1, GDA, YBX1, CRMP1, and CRMP2. In other cases, each of the different peptides in the kit binds to at least 2, 3, 4, 5, 6, or 7 different maternal antibodies, e.g., the different peptides bind to maternal antibodies against 2, 3, 4, 5, 6, or all 7 of the following antigens: LDH A, LDH B, STIP1, GDA, YBX1, CRMP1, and CRMP2.

In certain embodiments, the kit further comprises instructions for use. In some instances, the instructions for use include instructions for contacting the solid support with a biological sample from the mother or potential mother. In other instances, the instructions for use include instructions for correlating the presence of maternal antibodies that bind to one or more peptides with an increased risk of an offspring (e.g., fetus or child) at developing an ASD. In other embodiments, the kit further comprises labeled secondary antibodies for detecting the presence of maternal antibodies that bind to one or more peptides.

In other embodiments, the kit further comprises negative and positive control samples. In some instances, the negative control samples are obtained from mothers who have typically developing (TD) children. In other instances, the biological sample and/or the control samples are reactive to 1, 2, 3, 4, 5, 6, or all 7 of the following full-length antigens: LDH A, LDH B, STIP1, GDA, YBX1, CRMP1, and CRMP2. In yet other instances, neither the biological nor the control samples is reactive to any the full-length antigens LDH A, LDH B, STIP1, GDA, YBX1, CRMP1, or CRMP2.

In further embodiments, the kit further comprises a secondary antibody labeled directly or indirectly with a detectable moiety.

In a further aspect, provided herein is a method for determining a risk of an offspring for developing an autism spectrum disorder (ASD), the method comprising: detecting in a biological sample from the mother or potential mother of the offspring the presence or absence of maternal antibodies that bind to any one of the peptides described herein or a plurality thereof, wherein the presence of maternal antibodies that bind to the peptide or plurality thereof indicates an increased risk of the offspring for developing an ASD. The method can also include obtaining the sample from the mother or potential mother. The sample can be selected from the group consisting of blood, serum, plasma, amniotic fluid, milk, and saliva.

In some embodiments, the plurality of peptides used to detect the maternal antibodies comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 different peptides, e.g., selected from SEQ ID NOS:1-96 and mimotopes thereof. In certain instances, the peptides may be derived from the same antigen and bind to the same maternal antibodies. In other instances, the peptides may be derived from different antigens and bind to different maternal antibodies. In yet other instances, the peptides may comprise a combination of peptides that bind to the same maternal antibodies and peptides that bind to one or more additional maternal antibodies. In some cases, each of the different peptides binds to the same maternal antibodies, e.g., all of the different peptides bind to maternal antibodies against a single antigen selected from LDH A, LDH B, STIP1, GDA, YBX1, CRMP1, and CRMP2. In other cases, each of the different peptides binds to at least 2, 3, 4, 5, 6, or 7 different maternal antibodies, e.g., the different peptides bind to maternal antibodies against 2, 3, 4, 5, 6, or all 7 of the following antigens: LDH A, LDH B, STIP1, GDA, YBX1, CRMP1, and CRMP2.

In some embodiments, the peptide or plurality thereof is attached to a solid support. Non-limiting examples of solid supports include a multiwell plate, an ELISA plate, a microarray, a chip, a bead, a porous strip, and a nitrocellulose filter. In certain instances, the maternal antibodies can be detected by a technique such as, e.g., ELISA, Western blot, dot blot, radioimmunoassay, immunoprecipitation, electrochemiluminescence, immunofluorescence, FACS analysis, or multiplex bead assay.

In some embodiments, the presence of maternal antibodies in the test sample (i.e., a biological sample from the mother or potential mother) is detected without comparing the test sample to a control sample. In other embodiments, the test sample is compared to a positive or negative control sample. In some instances, the test sample and/or the control sample is reactive to 1, 2, 3, 4, 5, 6, or all of the following full-length antigens: LDH A, LDH B, STIP1, GDA, YBX1, CRMP1, and CRMP2. In other instances, neither the test sample nor the control sample is reactive to any of the full-length antigens LDH A, LDH B, STIP1, GDA, YBX1, CRMP1, and CRMP2. In yet other instances, the negative control is obtained from a mother who has TD children.

In some embodiments, the mother or potential mother has a child with an ASD. In other embodiments, the mother or potential mother has a familial history of ASD or autoimmune disease.

In another aspect, provided herein is a method for preventing or reducing a risk of an offspring for developing an autism spectrum disorder (ASD), the method comprising: administering a therapeutically effective amount of any one of the peptides described herein or a plurality thereof to the mother or potential mother of the offspring, wherein the peptide or plurality thereof binds to maternal antibodies circulating in the mother or potential mother to form neutralizing complexes, thereby preventing or reducing the risk of the offspring for developing an ASD. In particular embodiments, the peptides block the binding between the maternal antibodies and their antigenic polypeptides.

In some embodiments, the method further includes removing the neutralizing complexes from the mother or potential mother. In certain instances, the neutralizing complexes are removed by affinity plasmapheresis. In other embodiments, the peptide or plurality of peptides is administered intravenously.

In some embodiments, the plurality of peptides administered to block the binding of the maternal antibodies to their antigens comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 different peptides, e.g., selected from SEQ ID NOS:1-96 and mimotopes thereof. In certain instances, the peptides may be derived from the same antigen and bind to the same maternal antibodies. In other instances, the peptides may be derived from different antigens and bind to different maternal antibodies. In yet other instances, the peptides may comprise a combination of peptides that bind to the same maternal antibodies and peptides that bind to one or more additional maternal antibodies. In some cases, each of the different peptides binds to the same maternal antibodies, e.g., all of the different peptides bind to maternal antibodies against a single antigen selected from LDH A, LDH B, STIP1, GDA, YBX1, CRMP1, and CRMP2. In other cases, each of the different peptides binds to at least 2, 3, 4, 5, 6, or 7 different maternal antibodies, e.g., the different peptides bind to maternal antibodies against 2, 3, 4, 5, 6, or all 7 of the following antigens: LDH A, LDH B, STIP1, GDA, YBX1, CRMP1, and CRMP2.

Other objects, features, and advantages of the present invention will be apparent to one of skill in the art from the following detailed description.

BRIEF DESCRIPTION OF THE DRAWINGS

None

DETAILED DESCRIPTION OF THE INVENTION

I. Introduction

Autism spectrum disorders (ASD) are severe neurodevelopmental disorders affecting as many as 1 in 150 children. The presence of maternal IgG antibodies with specificity for human fetal brain proteins at molecular weights of approximately 37 kDa, 39 kDa and 73 kDa in a subset of mothers of children with an ASD has been described. See, e.g., U.S.

Pat. No. 7,452,681. The present invention is based, in part, on the identification of peptides (e.g., peptide epitopes) that specifically bind to maternal autoantibodies that are indicative of an increased risk that an offspring such as a fetus or child will develop an ASD. The peptide epitopes described herein include those for lactate dehydrogenase A (LDH A), lactate dehydrogenase B (LDH B), stress-induced phosphoprotein 1 (STIP1), guanine deaminase (GDA), Y Box Binding Protein 1 (YBX1), collapsin response mediator protein 1 (CRMP1), and collapsin response mediator protein 2 (CRMP2). The presence of maternal autoantibodies against one or more of the peptide epitopes in a biological sample of the mother or potential mother is indicative of an increased risk of the offspring developing an ASD. The peptide epitopes or mimotopes thereof can also be administered to the mother or potential mother to block the binding between maternal autoantibodies and their antigens, thereby neutralizing the maternal autoantibodies, and the neutralized complexes comprising the peptide epitopes bound to the maternal autoantibodies are optionally removed using an extracorporeal therapy, such as affinity plasmapheresis.

II. Definitions

As used herein, the following terms have the meanings ascribed to them unless specified otherwise.

The terms "autism spectrum disorder," "autistic spectrum disorder," "autism" or "ASD" refer to a spectrum of neurodevelopmental disorders characterized by impaired social interaction and communication accompanied by repetitive and stereotyped behavior. Autism includes a spectrum of impaired social interaction and communication, however, the disorder can be roughly categorized into "high functioning autism" or "low functioning autism," depending on the extent of social interaction and communication impairment. Individuals diagnosed with "high functioning autism" have minimal but identifiable social interaction and communication impairments (i.e., Asperger's syndrome). Additional information on autism spectrum disorders can be found in, for example, Autism Spectrum Disorders: A Research Review for Practitioners, Ozonoff, et al., eds., 2003, American Psychiatric Pub; Gupta, Autistic Spectrum Disorders in Children, 2004, Marcel Dekker Inc; Hollander, Autism Spectrum Disorders, 2003, Marcel Dekker Inc; Handbook of Autism and Developmental Disorders, Volkmar, ed., 2005, John Wiley; Sicile-Kira and Grandin, Autism Spectrum Disorders: The Complete Guide to Understanding Autism, Asperger's Syndrome, Pervasive Developmental Disorder, and Other ASDs, 2004, Perigee Trade; and Duncan, et al., Autism Spectrum Disorders [Two Volumes]: A Handbook for Parents and Professionals, 2007, Praeger.

The terms "typically developing" and "TD" refer to a subject who has not been diagnosed with an autism spectrum disorder (ASD). Typically developing children do not exhibit the ASD-associated impaired communication abilities, impaired social interactions, or repetitive and/or stereotyped behaviors with a severity that is typically associated with a diagnosis of an ASD. While typically developing children may exhibit some behaviors that are displayed by children who have been diagnosed with an ASD, typically developing children do not display the constellation and/or severity of behaviors that supports a diagnosis of an ASD.

The term "lactate dehydrogenase" or "LDH" refers to an enzyme that catalyzes the interconversion of pyruvate and lactate with concomitant interconversion of NADH and NAD+. Lactate dehydrogenases exist in four distinct enzyme classes. Two of them are cytochrome c-dependent enzymes with each acting on either D-lactate (EC 1.1.2.4) or L-lactate (EC 1.1.2.3). The other two are NAD(P)-dependent enzymes with each acting on either D-lactate (EC 1.1.1.28) or L-lactate (EC 1.1.1.27). The LDH enzyme is composed of 4 subunits, wherein the subunits are either "M" or "H". The LDH A gene encodes the M subunit, known interchangeably LDH-M or LDH A. The LDH B gene encodes the H subunit, known interchangeably as LDH-H or LDH B. There are five LDH isozymes, each containing four subunits. The major LDH isozyme of skeletal muscle and liver, LDH-5 (M4), has four muscle (M) subunits; while LDH-1 (1-14) is the main isozyme for heart muscle in most species, containing 4 heart (H) subunits. The other variants contain both types of subunits, e.g., LDH-2 (H3Mi)—in the reticuloendothelial system, LDH-3 (H2M2)—in the lungs, and LDH-4 (HiM3)—in the kidneys. LDH-2 is the predominant form in the serum. LDHA is also known as LDH1, LDH muscle subunit, LDH-M, EC 1.1.1.27, renal carcinoma antigen NY-REN-59, Cell proliferation-inducing gene 19 protein, PIG19 and L-lactate dehydrogenase A chain; LDHB is also known as LDH2 or LDH-H or TRG-5; LDHC is testis specific. Non-limiting examples of LDH A amino acid sequences are set forth in GenBank Accession Nos. AAP36496.1, BAD96798.1, NM_005566.3- ->NP_005557.1 (isoform 1), NM_001135239.1- ->NP_001128711.1 (isoform 2), NM_001165414.1- ->NP_001158886.1 (isoform 3), NM_001165415.1- ->NP_001158887.1 (isoform 4), and NM_001165416.1- ->NP_001158888.1 (isoform 5). Non-limiting examples of LDH B amino acid sequences are set forth in GenBank Accession Nos. NM_002300.6- ->NP_002291.1 (variant 1) and NM_001174097.1- ->NP 001167568.1 (variant 2).

The term "collapsin response mediator protein 1" or "CRMP1" (also known as DRP1; DRP-1; CRMP-1; DPYSL1; ULIP-3) refers to a cytosolic phosphoprotein known to function in neuronal differentiation and axonal guidance. CRMP1 is a member of a family of cytosolic phosphoproteins expressed exclusively in the nervous system. The encoded protein is thought to be a part of the semaphorin signal transduction pathway implicated in semaphorin-induced growth cone collapse during neural development. Non-limiting examples of CRMP1 amino acid sequences are set forth in GenBank Accession Nos. NM_001014809.1- - ->NP_001014809.1 (isoform 1) and NM_001313.3- ->NP. 001304.1 (isoform 2).

The term "collapsin response mediator protein 2" or "CRMP2" (also known as DRP2; DRP-2; CRMP-2; DPYSL2; ULIP-2) refers to a cytosolic phosphoprotein known to function in neuronal development and polarity, axon growth and guidance, neuronal growth cone collapse and cell migration. CRMP2 is a member of a family of cytosolic phosphoproteins expressed exclusively in the nervous system. The encoded protein is thought to be a part of the semaphorin signal transduction pathway implicated in semaphorin-induced growth cone collapse during neural development. Non-limiting examples of CRMP2 amino acid sequences are set forth in GenBank Accession Nos. NM_001386.4- ->NP_001377.1 and BAD92432.

The term "Stress Induced Phosphoprotein 1" or "STIP1" (also known as Hsp70/Hsp90-organizing Protein (HOPI), STI1, STILL, IEF-SSP-3521 and P60) refers to an adaptor protein that assists in folding of HSP70 and HSP90. STIP1 also stimulates the ATPase activity of HSP70, while inhibiting the ATPase activity of HSP90, suggesting a regulatory role. Furthermore, STIP1 binds to the cellular prion protein PrPc and regulates short-term and long-term memory consolidation. A non-limiting example of a STIP1 amino acid sequence is set forth in GenBank Accession No. NM_006819.2- ->NP_006810.1.

The terms "guanine deaminase" and "GDA" (also known as Cypin, Guanase, KIAA1258, MGC9982 and Nedasin) refer to an enzyme that catalyzes the hydrolytic deamination of guanine, yielding xanthine and ammonia. GDA has also been shown to regulate PSD-95 postsynaptic targeting. A non-limiting example of a GDA amino acid sequence is set forth in GenBank Accession No. NM_004293.3- ->NP_004284.1.

The terms "Y Box Binding Protein 1" and "YBX1" (also known as BP-8, CSDA2, CSDB, DBPB, MDR-NF1, MGC104858, MGC110976, MGC117250, NSEP-1, NSEP1, YB-1 and YB1) refer to a protein that mediates pre-mRNA alternative splicing regulation. YBX1 binds to splice sites in pre-mRNA and regulates splice site selection; binds and stabilizes cytoplasmic mRNA; contributes to the regulation of translation by modulating the interaction between the mRNA and eukaryotic initiation factors; binds to promoters that contain a Y-box (5'-CTGATTGGCCAA-3' (SEQ ID NO: 119)), e.g., found in HLA class II genes; and promotes the separation of DNA strands that contain mismatches or are modified by cisplatin. A non-limiting example of a YBX1 amino acid sequence is set forth in GenBank Accession No. NM_004559.3- ->NP 004550.2.

The term "isolated," when applied to a nucleic acid or protein, denotes that the nucleic acid or protein is essentially free of other cellular components with which it is associated in the natural state. It is preferably in a homogeneous state. It can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "polypeptide," "peptide," and "protein" are used interchangeably herein to refer to a polymer of amino acid residues, or an assembly of multiple polymers of amino acid residues. The terms apply to amino acid polymers in which one or more amino acid residue is an artificial chemical mimic of a corresponding naturally occurring amino acid, as well as to naturally occurring amino acid polymers and non-naturally occurring amino acid polymer.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol (e.g., D-Arg for D-arginine) or by a lower-case one-letter amino acid symbol (e.g., r for D-arginine).

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins,* 1993).

The term "amino acid modification" or "amino acid alteration" refers to a substitution, a deletion, or an insertion of one or more amino acids.

"Percentage of sequence identity" is determined by comparing two optimally aligned sequences over a comparison window, wherein the portion of the sequence (e.g., a peptide of the invention) in the comparison window may comprise additions or deletions (i.e., gaps) as compared to the reference sequence which does not comprise additions or deletions, for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more polypeptide or peptide sequences, refer to two or more sequences or subsequences that are the same sequences. Two sequences are "substantially identical" if two sequences have a specified percentage of amino acid residues that are the same (i.e., 70%, 75%, 80%, 85%, 90%, 95%, 96%, 97%, 98% or 99% sequence identity over a specified region, or, when not specified, over the entire sequence of a reference sequence), when compared and aligned for maximum correspondence over a comparison window, or designated region as measured using one of the following sequence comparison algorithms or by manual alignment and visual inspection. With respect to amino acid sequences, identity or substantial identity can exist over a region that is at least 5, 10, 15 or 20 amino acids in length, optionally at least about 25, 30, 35, 40, 50, 75 or 100 amino acids in length, optionally at least about 150, 200 or 250 amino acids in length, or over the full length of the reference sequence. With respect to shorter amino acid sequences, e.g., amino acid sequences of 20 or fewer amino acids, substantial identity exists when one or two amino acid residues are conservatively substituted, according to the conservative substitutions defined herein.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Two examples of algorithms that are suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information.

An indication that two polypeptide or peptide sequences are substantially identical occurs when a first polypeptide or peptide is immunologically cross-reactive with the antibodies raised against a second polypeptide or peptide. Thus, a first polypeptide or peptide is typically substantially identical to a second polypeptide or peptide, for example, where the two sequences differ only by conservative substitutions.

The term "antigenic fragment" refers to a contiguous subsequence of a polypeptide that binds to an antibody. An antigenic fragment may or may not be immunogenic, i.e., it may or may not induce an immune response.

The term "conformational antigenic fragment" refers to a spatially contiguous region of a polypeptide or tetramer which may or may not be formed by a contiguous subsequence. A conformational antigenic fragment may or may not be immunogenic.

The term "epitope" or "antigenic determinant" refers to a site on a peptide or polypeptide to which B and/or T cells respond. B-cell epitopes can be formed both from contiguous amino acids or noncontiguous amino acids juxtaposed by tertiary or quaternary folding of a protein. Epitopes formed from contiguous amino acids are typically retained on exposure to denaturing solvents whereas epitopes formed by tertiary or quaternary folding (i.e., conformationally determined) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen (e.g., an electrochemiluminescence assay, a competitive ELISA, a solid phase radioimmunoassay (SPRIA) or a blocking Western blot). T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis. 170, 1110-19 (1994)), by antigen-dependent killing (cytotoxic T lymphocyte assay, Tigges et al., J. Immunol. (1996) 156:3901-3910) or by cytokine secretion. The epitopes of human testis-specific lactate dehydrogenase have been deduced from a cDNA sequence. See, Millan et al., *Proc. Natl Acad Sci,* (1987), 84(15):5311-5315.

The terms "bind(s) specifically" or "specifically directed against" refers to the preferential association between T-cell receptors and/or antibodies, in whole or part, with a target peptide/polypeptide or an antigenic fragment thereof in comparison to other peptides/polypeptides. It is, of course, recognized that a certain degree of non-specific interaction may occur between an antibody or T-cell receptor and a non-target peptide/polypeptide. Nevertheless, specific binding, may be distinguished as mediated through specific recognition of the target peptide/polypeptide or an antigenic fragment thereof. Typically, specific binding or a specifically directed immune response results in a much stronger association between the target peptide/polypeptide and an antibody against the target peptide/polypeptide or T-cell receptor than between an antibody against the target peptide/polypeptide or T-cell receptor and a non-target peptide/polypeptide. Specific binding typically results in greater than about 10-fold and most preferably greater than 100-fold increase in amount of bound antibody (per unit time) against the target polypeptide to a cell or tissue bearing the target polypeptide as compared to a cell or tissue lacking an epitope of the target polypeptide. Specific binding between the target polypeptide and an antibody against the target polypeptide generally means an affinity of at least $10^6$ $M^{-1}$. Affinities greater than $10^8$ $M^{-1}$ are preferred. Specific binding can be determined using any assay for antibody binding known in the art, including without limitation, Western blot, dot blot, ELISA, flow cytometry, electrochemilumines-cence, multiplex bead assay (e.g., using Luminex or fluo-rescent microbeads), and immunohistochemistry. T-cells specifically directed against an epitope of a target polypep-tide typically exhibit antigen-induced proliferation in response to the target polypeptide that is greater than about 2-fold, and more preferably greater than about 5-fold or 10-fold than antigen-induced proliferation in response to a non-target polypeptide. T cell proliferation assays are known in the art can be measured by $^3$H-thymidine incorporation.

The term "sample" refers to any biological specimen obtained from a subject, e.g., a human subject. Samples include, without limitation, whole blood, plasma, serum, red blood cells, white blood cells, saliva, urine, stool, sputum, bronchial lavage fluid, tears, nipple aspirate, breast milk, any other bodily fluid, a tissue sample such as a biopsy of a placenta, and cellular extracts thereof. In some embodi-ments, the sample is whole blood or a fractional component thereof, such as plasma, serum, or a cell pellet.

The term "subject," "individual," or "patient" typically includes humans, but can also include other animals such as, e.g., other primates, rodents, canines, felines, equines, ovines, porcines, and the like. In preferred embodiments, the subject is a human subject.

The term "increased risk of developing an ASD" refers to an increased likelihood or probability that a fetus or child exposed to antibodies that bind to one or more antigens described herein (e.g., lactate dehydrogenase A (LDH A), lactate dehydrogenase B (LDH B), stress-induced phospho-protein 1 (STIP1), guanine deaminase (GDA), Y Box Bind-ing Protein 1 (YBX1), collapsin response mediator protein 1 (CRMP1), and collapsin response mediator protein 2 (CRMP2)) or to levels of antibodies against one or more of the antigens above a predetermined threshold level will develop symptoms of an ASD in comparison to the risk, likelihood or probability of a fetus or child that has not been exposed to antibodies against the one or more antigens or to levels of antibodies against the one or more antigens that are below a predetermined threshold level.

The term "reduced risk of developing an ASD" refers to the decreased likelihood or probability that a fetus or child exposed to antibodies against one or more antigens described herein (e.g., LDH A, LDH B, STIP1, GDA, YBX1, CRMP1, and CRMP2) or to levels of antibodies against one or more of the antigens above a predetermined threshold level, and whose mother has received therapeutic intervention, e.g., to block, inactivate or remove antibodies that bind to the antigens, will develop symptoms of an ASD in comparison to the likelihood or probability that a fetus or child exposed to antibodies against the antigens or to levels of antibodies against the one or more antigens above a predetermined threshold level and whose mother has not received therapeutic intervention will develop symptoms of an ASD.

The term "peptide epitope" or "antigenic peptide" refers to peptides or fragments of one or more antigens described herein (e.g., LDH A, LDH B, STIP1, GDA, YBX1, CRMP1, and CRMP2) that imitate an epitope (e.g., bound by an antibody against the antigen), although no clear homology may exist between the structure or sequence of such peptide epitopes and the epitope of the native antigen. Instead, mimicry of a peptide epitope relies on similarities in phys-icochemical properties and similar spatial organization. The screening and construction of peptide epitopes is known in the art. For example, peptide epitopes can be derived from known epitopes by sequence modification or developed de novo using combinatorial peptide libraries for peptides, e.g., that bind to antibodies against the one or more antigens. See, e.g., Yip and Ward, Comb Chem High Throughput Screen (1999) 2(3):125-128; Sharav, et al, Vaccine (2007) 25(16):3032-37; and Knittelfelder, et al., Expert Opin Biol Then (2009) 9(4):493-506.

The term "familial history" refers to the presence of a disease condition (e.g., an ASD or an autoimmune disease) in a family member. The family member can be of direct lineage, e.g., a parent, a child or a grandparent or a close relation, e.g., a sibling, an aunt or uncle, a cousin. Typically the family member is a blood relative with a common genetic heritage.

The term "therapeutically effective amount" refers to the amount of a peptide of the invention that is capable of achieving a therapeutic effect or the desired result (i.e., a sufficient amount of peptide to block binding of antibodies against the antigen to the target antigen), preferably with minimal or no side-effects. In some embodiments, a thera-peutically acceptable amount does not induce or cause undesirable side-effects. A therapeutically effective amount can be determined by first administering a low dose, and then incrementally increasing that dose until the desired effect is achieved. A "prophylactically effective amount" and a "therapeutically effective amount" of an antibody blocking agent of the invention can prevent the onset of or result in a decrease in severity of an ASD. A "prophylactically effective amount" and a "therapeutically effective amount" can also prevent or ameliorate, respectively, impairment or disability due to the disorders and diseases resulting from the activity of maternal antibodies.

The term "pharmaceutically acceptable carrier" refers to a compound, chemical, or molecule that is useful in prepar-ing a pharmaceutical composition that is generally safe, non-toxic, and neither biologically nor otherwise undesir-able and includes that which is acceptable for pharmaceu-tical use in a subject. Suitable pharmaceutical carriers are described herein and in "Remington's Pharmaceutical Sci-ences" by E. W. Martin.

As used herein, the term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a peptide of the invention for preventing or relieving one or more symptoms associated with the presence or activity of maternal antibodies. By "co-administer" it is meant that a peptide of the invention is administered at the same time, just prior to, or just after the administration of a second drug.

As used herein, the term "treating" refers to any indicia of success in the treatment or amelioration of a pathology or condition, including any objective or subjective parameter such as abatement, remission, diminishing of symptoms or making the pathology or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, histopathological examination (e.g., analysis of biopsied tissue), laboratory analysis of urine, saliva, tissue sample, serum, plasma, or blood, or imaging.

The term "specifically inhibit(s)" refers to the ability of an agent (e.g., a peptide epitope) to inhibit the binding of antibodies against one or more antigens (e.g., LDH A, LDH B, STIP1, GDA, YBX1, CRMP1, and CRMP2). Specific inhibition typically results in at least about a 2-fold inhibition over background, for example, greater than about 10-fold, 20-fold, 50-fold inhibition of binding of antibodies against the target antigen, for example, by comparing the binding of the antibodies in the absence of the agent. In some embodiments, the binding of antibodies to the target antigen is completely inhibited or blocked by the peptide epitope. Typically, specific inhibition is a statistically meaningful reduction in antibody binding to the target antigen (e.g., p<0.05) using an appropriate statistical test.

The term "agent" includes peptide epitopes, mimotopes, polypeptides (e.g., ligands, antibodies), nucleic acids, small organic compounds, and the like.

The term "solid support" refers to any material suitable for performing the methods of the invention, such as plastic or glass tubes, beads, slides, microtiter plates, porous filters or membranes, non-porous filters or membranes, nonmagnetic beads, microbeads, slides, microarrays, and the like.

The term "neutralizing complex" refers to a complex comprising a maternal antibody bound to a specific peptide epitope that prevents/inhibits/blocks the maternal antibody from binding to its antigen (e.g., LDH A, LDH B, STIP1, GDA, YBX1, CRMP1, and CRMP2). For instance, a maternal autoantibody that specifically recognizes the CRMP1 antigen (e.g., the CRMP1 protein represented by NCBI RefSeq No.: NP_001304.1) can form a neutralizing complex with a CRMP1 peptide epitope described herein or mimotope thereof, such that the maternal autoantibody does not bind to the CRMP1 antigen.

The term "affinity plasmapheresis" refers to an extracorporeal blood purification procedure for the removal of deleterious agents (e.g., disease-causing agents) from the plasma of a subject.

III. Detailed Description of the Embodiments

The present invention provides peptides (e.g., peptide epitopes and mimotopes thereof) that specifically bind to maternal autoantibodies against endogenous autoantigens including lactate dehydrogenase A (LDH A), lactate dehydrogenase B (LDH B), stress-induced phosphoprotein 1 (STIP1), guanine deaminase (GDA), Y Box Binding Protein 1 (YBX1), collapsin response mediator protein 1 (CRMP1), and collapsin response mediator protein 2 (CRMP2). The present invention also provides compositions and kits comprising the peptides described herein. In addition, the present invention provides methods for determining a risk of a child or future offspring (e.g., in a mother or a potential mother who is pregnant or prior to conception) for developing an autism spectrum disorder (ASD) by detecting the presence of maternal autoantibodies in a biological sample of the mother or potential mother using the peptides described herein. The present invention further provides methods for preventing or reducing a risk of an offspring for developing an ASD by administering a therapeutically effective amount of the peptides described herein to the mother or potential mother of the offspring to block the binding between maternal autoantibodies and their antigens.

A. Peptide Epitopes

In certain aspects, the present invention provides isolated peptides that specifically bind to maternal antibodies that are generated in the mother or potential mother against one or more polypeptides selected from lactate dehydrogenase A (LDH A), lactate dehydrogenase B (LDH B), stress-induced phosphoprotein 1 (STIP1), guanine deaminase (GDA), Y Box Binding Protein 1 (YBX1), collapsin response mediator protein 1 (CRMP1), and collapsin response mediator protein 2 (CRMP2).

In a first aspect, the peptide has at least about 50%, e.g., about 50%, 55%, 60%, 65%, 70%, 75%, 80%, 85%, 90%, 95%, 96%, 97%, 98% or 99% sequence identity to the amino acid sequence of any one of SEQ ID NOS:1-7 and 62-64. In some embodiments, the peptide comprises at least about 5, 6, 7, 8, 9, 10, 11, 12, 13, 14, or 15 contiguous amino acids of the amino acid sequence of any one of SEQ ID NOS:1-7 and 62-64. In other embodiments, the peptide (e.g., an antigenic fragment thereof) has at least about 50%, e.g., about 50%, 55%, 60%, 65%, 70%, 75%, 80%, 85%, 90%, 95%, 96%, 97%, 98% or 99% of the length of the amino acid sequence of any one of SEQ ID NOS:1-7 and 62-64. In some embodiments, the peptide comprises an amino acid sequence comprising or consisting of the amino acid sequence of any one of SEQ ID NOS:1-7 and 62-64. In other embodiments, the peptide comprises one or more additional amino acid residues at the amino-terminus and/or carboxyl-terminus that correspond to the amino acid residues at those positions in a lactate dehydrogenase A (LDH A) polypeptide sequence. In certain embodiments, the peptide comprises an amino acid sequence selected from VDVIEDK (SEQ ID NO:97) and VHPVSTMIK (SEQ ID NO:98). In particular embodiments, the peptide binds to a maternal antibody that binds to an LDH A polypeptide.

In a second aspect, the peptide has at least about 50%, e.g., about 50%, 55%, 60%, 65%, 70%, 75%, 80%, 85%, 90%, 95%, 96%, 97%, 98% or 99% sequence identity to the amino acid sequence of any one of SEQ ID NOS:8-19 and 65-72. In some embodiments, the peptide comprises at least about 5, 6, 7, 8, 9, 10, 11, 12, 13, 14, or 15 contiguous amino acids of the amino acid sequence of any one of SEQ ID NOS:8-19 and 65-72. In other embodiments, the peptide (e.g., an antigenic fragment thereof) has at least about 50%, e.g., about 50%, 55%, 60%, 65%, 70%, 75%, 80%, 85%, 90%, 95%, 96%, 97%, 98% or 99% of the length of the amino acid sequence of any one of SEQ ID NOS:8-19 and 65-72. In some embodiments, the peptide comprises an amino acid sequence comprising or consisting of the amino acid sequence of any one of SEQ ID NOS:8-19 and 65-72. In other embodiments, the peptide comprises one or more additional amino acid residues at the amino-terminus and/or carboxyl-terminus that correspond to the amino acid residues at those positions in a lactate dehydrogenase B (LDH B) polypeptide sequence. In certain embodiments, the peptide comprises an amino acid sequence selected from PVAEEEATVPNN (SEQ ID NO:99), IIVVSNPVDILT (SEQ ID NO:100), TPKIVADKDYSVT (SEQ ID NO:101), and MLKNLSRIHPVST (SEQ ID NO:102). In particular embodiments, the peptide binds to a maternal antibody that binds to an LDH B polypeptide.

In a third aspect, the peptide has at least about 50%, e.g., about 50%, 55%, 60%, 65%, 70%, 75%, 80%, 85%, 90%, 95%, 96%, 97%, 98% or 99% sequence identity to the amino acid sequence of any one of SEQ ID NOS:20-23 and 73-76. In some embodiments, the peptide comprises at least about 5, 6, 7, 8, 9, 10, 11, 12, 13, 14, or 15 contiguous amino acids of the amino acid sequence of any one of SEQ ID NOS: 20-23 and 73-76. In other embodiments, the peptide (e.g., an antigenic fragment thereof) has at least about 50%, e.g., about 50%, 55%, 60%, 65%, 70%, 75%, 80%, 85%, 90%, 95%, 96%, 97%, 98% or 99% of the length of the amino acid sequence of any one of SEQ ID NOS:20-23 and 73-76. In some embodiments, the peptide comprises an amino acid sequence comprising or consisting of the amino acid sequence of any one of SEQ ID NOS:20-23 and 73-76. In other embodiments, the peptide comprises one or more additional amino acid residues at the amino-terminus and/or carboxyl-terminus that correspond to the amino acid residues at those positions in a stress-induced phosphoprotein 1 (STIP1) polypeptide sequence. In certain embodiments, the peptide comprises an amino acid sequence selected from VDLGSMDEEEE (SEQ ID NO:103) and PPPPPKKETK-PEPME (SEQ ID NO:104). In particular embodiments, the peptide binds to a maternal antibody that binds to a STIP1 polypeptide.

In a fourth aspect, the peptide has at least about 50%, e.g., about 50%, 55%, 60%, 65%, 70%, 75%, 80%, 85%, 90%, 95%, 96%, 97%, 98% or 99% sequence identity to the amino acid sequence of any one of SEQ ID NOS:24-27 and 77-79. In some embodiments, the peptide comprises at least about 5, 6, 7, 8, 9, 10, 11, 12, 13, 14, or 15 contiguous amino acids of the amino acid sequence of any one of SEQ ID NOS: 24-27 and 77-79. In other embodiments, the peptide (e.g., an antigenic fragment thereof) has at least about 50%, e.g., about 50%, 55%, 60%, 65%, 70%, 75%, 80%, 85%, 90%, 95%, 96%, 97%, 98% or 99% of the length of the amino acid sequence of any one of SEQ ID NOS:24-27 and 77-79. In some embodiments, the peptide comprises an amino acid sequence comprising or consisting of the amino acid sequence of any one of SEQ ID NOS:24-27 and 77-79. In other embodiments, the peptide comprises one or more additional amino acid residues at the amino-terminus and/or carboxyl-terminus that correspond to the amino acid residues at those positions in a guanine deaminase (GDA)

polypeptide sequence. In particular embodiments, the peptide binds to a maternal antibody that binds to a GDA polypeptide.

In a fifth aspect, the peptide has at least about 50%, e.g., about 50%, 55%, 60%, 65%, 70%, 75%, 80%, 85%, 90%, 95%, 96%, 97%, 98% or 99% sequence identity to the amino acid sequence of any one of SEQ ID NOS:28-35 and 80-83. In some embodiments, the peptide comprises at least about 5, 6, 7, 8, 9, 10, 11, 12, 13, 14, or 15 contiguous amino acids of the amino acid sequence of any one of SEQ ID NOS: 28-35 and 80-83. In other embodiments, the peptide (e.g., an antigenic fragment thereof) has at least about 50%, e.g., about 50%, 55%, 60%, 65%, 70%, 75%, 80%, 85%, 90%, 95%, 96%, 97%, 98% or 99% of the length of the amino acid sequence of any one of SEQ ID NOS:28-35 and 80-83. In some embodiments, the peptide comprises an amino acid sequence comprising or consisting of the amino acid sequence of any one of SEQ ID NOS:28-35 and 80-83. In other embodiments, the peptide comprises one or more additional amino acid residues at the amino-terminus and/or carboxyl-terminus that correspond to the amino acid residues at those positions in a Y box binding protein 1 (YBX1) polypeptide sequence. In certain embodiments, the peptide comprises an amino acid sequence selected from TVKWFNVRN (SEQ ID NO:105), FNVRN (SEQ ID NO:106), and FNVRNGYGFIN (SEQ ID NO:107). In particular embodiments, the peptide binds to a maternal antibody that binds to a YBX1 polypeptide.

In a sixth aspect, the peptide has at least about 50%, e.g., about 50%, 55%, 60%, 65%, 70%, 75%, 80%, 85%, 90%, 95%, 96%, 97%, 98% or 99% sequence identity to the amino acid sequence of any one of SEQ ID NOS:36-44 and 84-88. In some embodiments, the peptide comprises at least about 5, 6, 7, 8, 9, 10, 11, 12, 13, 14, or 15 contiguous amino acids of the amino acid sequence of any one of SEQ ID NOS: 36-44 and 84-88. In other embodiments, the peptide (e.g., an antigenic fragment thereof) has at least about 50%, e.g., about 50%, 55%, 60%, 65%, 70%, 75%, 80%, 85%, 90%, 95%, 96%, 97%, 98% or 99% of the length of the amino acid sequence of any one of SEQ ID NOS:36-44 and 84-88. In some embodiments, the peptide comprises an amino acid sequence comprising or consisting of the amino acid sequence of any one of SEQ ID NOS:36-44 and 84-88. In other embodiments, the peptide comprises one or more additional amino acid residues at the amino-terminus and/or carboxyl-terminus that correspond to the amino acid residues at those positions in a collapsin response mediator protein 1 (CRMP1) polypeptide sequence. In certain embodiments, the peptide comprises an amino acid sequence selected from VPATPKYATPAP (SEQ ID NO:108) and TSFEK (SEQ ID NO:109). In particular embodiments, the peptide binds to a maternal antibody that binds to a CRMP1 polypeptide.

In a seventh aspect, the peptide has at least about 50%, e.g., about 50%, 55%, 60%, 65%, 70%, 75%, 80%, 85%, 90%, 95%, 96%, 97%, 98% or 99% sequence identity to the amino acid sequence of any one of SEQ ID NOS:45-61 and 89-96. In some embodiments, the peptide comprises at least about 5, 6, 7, 8, 9, 10, 11, 12, 13, 14, or 15 contiguous amino acids of the amino acid sequence of any one of SEQ ID NOS:45-61 and 89-96. In other embodiments, the peptide (e.g., an antigenic fragment thereof) has at least about 50%, e.g., about 50%, 55%, 60%, 65%, 70%, 75%, 80%, 85%, 90%, 95%, 96%, 97%, 98% or 99% of the length of the amino acid sequence of any one of SEQ ID NOS:45-61 and 89-96. In some embodiments, the peptide comprises an amino acid sequence comprising or consisting of the amino acid sequence of any one of SEQ ID NOS:45-61 and 89-96. In other embodiments, the peptide comprises one or more additional amino acid residues at the amino-terminus and/or carboxyl-terminus that correspond to the amino acid residues at those positions in a collapsin response mediator protein 2 (CRMP2) polypeptide sequence. In certain embodiments, the peptide comprises an amino acid sequence selected from VPEPGTSLLAAFDQ (SEQ ID NO:110), KTISAKTHNSSLEY (SEQ ID NO:111), HNSL-LEY (SEQ ID NO:112), RGVPRGLYDGPVC (SEQ ID NO:113), VPRGLYDGPVC (SEQ ID NO:114), and VPR-GLYDGPVCEVS (SEQ ID NO:115). In particular embodiments, the peptide binds to a maternal antibody that binds to a CRMP2 polypeptide.

In some embodiments, the peptide is between about 5 to about 45 amino acids in length, between about 8 to about 45 amino acids in length, between about 8 to about 25 amino acids in length, between about 12 to about 45 amino acids in length, between about 5 to about 40 amino acids in length, between about 10 to about 40 amino acids in length, between about 15 to about 30 amino acids in length, between about 15 to about 25 amino acids in length, or about 45, 40, 35, 30, 25, 20, 15, 10, or 5 amino acids in length. For example, the peptide may be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more amino acids in length. Typically, the peptide should not exceed a length which would allow the formation of a tertiary structure, such as, for example, greater than 45 amino acids if present as an isolated molecule. However, the peptide may exceed 45 amino acids if fused to a larger molecule such as an antibody or another protein or macromolecule which could prevent the formation of a tertiary structure within the peptide. The peptide may also exceed 45 amino acids if it is a bivalent peptide having first and second peptide fragments that bind to different maternal antibodies. In particular embodiments, the peptide is up to about 15, 20, 25, 30, 35, 40, or 45 amino acids in length.

In some embodiments, the peptide further comprises a label such as a detectable label. In certain instances, the label is selected from the group consisting of biotin, a fluorescent label, a chemiluminescent label, and a radioactive label. In certain other instances, the label is covalently attached to the peptide.

In other embodiments, the peptide includes variants that are further modified to improve their resistance to proteolytic degradation or to optimize solubility properties or to render them more suitable as a therapeutic agent. For example, the peptide further includes analogs containing residues other than naturally occurring L-amino acids, e.g., D-amino acids or non-naturally occurring synthetic amino acids. D-amino acids may be substituted for some or all of the amino acid residues.

In certain embodiments, the peptide comprises naturally-occurring amino acids and/or unnatural amino acids. Examples of unnatural amino acids include, but are not limited to, D-amino acids, ornithine, diaminobutyric acid ornithine, norleucine ornithine, pyriylalanine, thienylalanine, naphthylalanine, phenylglycine, alpha and alpha-disubstituted amino acids, N-alkyl amino acids, lactic acid, halide derivatives of naturally-occurring amino acids (e.g., trifluorotyrosine, p-Cl-phenylalanine, p-Br-phenylalanine, p-I-phenylalanine, etc.), L-allyl-glycine, b-alanine, L-α-amino butyric acid, L-g-amino butyric acid, L-α-amino isobutyric acid, L-e-amino caproic acid, 7-amino heptanoic acid, L methionine sulfone, L-norleucine, L-norvaline, p-nitro-L- phenylalanine, L-hydroxyproline, L-thioproline, methyl derivatives of phenylalanine (e.g., 1-methyl-Phe, pentamethyl-Phe, L-Phe (4-amino), L-Tyr (methyl), L-Phe (4-isopropyl), L-Tic (1,2,3,4-tetrahydroisoquinoline-3-carboxyl acid), L-diaminopropionic acid, L-Phe (4-benzyl), etc.). The peptide may be further modified. For example, one or more amide bonds may be replaced by ester or alkyl backbone bonds. There may be N- or C-alkyl substituents, side-chain modifications, or constraints such as disulfide bridges or side-chain amide or ester linkages.

In some embodiments, the peptide includes both modified peptides and synthetic peptide analogues. Peptides may be modified to improve formulation and storage properties, or to protect labile peptide bonds by incorporating non-peptidic structures.

In other embodiments, the peptide may be cyclized. Methods are well known in the art for introducing cyclic structures into peptides to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclization methods include the formation of thioethers and carboxyl- and amino- terminal amides and esters. A number of synthetic techniques have been developed to generate synthetic circular peptides (see, e.g., Tarn et al., *Protein Sci.*, 7:1583-1592 (1998); Romanovskis et al., *J. Pept. Res.*, 52: 356-374 (1998); Camarero et al., *J. Amer. Chem. Soc.*, 121: 5597-5598 (1999); Valero et al., *J. Pept. Res.*, 53(1): 56-67 (1999)). Generally, the role of cyclizing peptides is twofold: (1) to reduce hydrolysis in vivo; and (2) to thermodynamically destabilize the unfolded state and promote secondary structure formation.

In some embodiments, the present invention comprises a plurality of peptides that includes at least two of the same peptide or different peptides linked covalently or non-covalently. For example, in some embodiments, at least two, three, four, five, or six of the same peptide or different peptides are linked covalently, e.g., so that they will have the appropriate size and/or binding properties, but avoiding unwanted aggregation.

The peptides of the present invention can be produced by any suitable means known or later discovered in the field, e.g., synthesized in vitro, purified or substantially purified from a natural source, recombinantly produced from eukaryotic or prokaryotic cells, etc.

The peptides may be prepared by in vitro synthesis, using conventional methods as known in the art. For example, peptides may be produced by chemical synthesis, e.g., using solid phase techniques and/or automated peptide synthesizers. In certain instances, peptides may be synthesized using solid phase strategies on an automated multiple peptide synthesizer (Abimed AMS 422) using 9-fluorenylmethyl-oxycarbonyl (Fmoc) chemistry. The peptides can then be purified by reversed phase-HPLC and lyophilized. By using synthesizers, naturally-occurring amino acids may be substituted with unnatural amino acids. The particular sequence and the manner of preparation will be determined by convenience, economics, purity required, and the like. The peptides may alternatively be prepared by cleavage of a longer peptide or full-length protein sequence.

The peptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. Methods which are well known to those skilled in the art can be used to construct expression vectors containing coding sequences and appropriate transcriptional/translational control signals. These methods include, for example, in vitro recombinant DNA techniques, synthetic techniques, and in vivo recombination/genetic recombination. Alternatively, RNA capable of encoding the peptides of interest may be chemically synthesized. One of skill in the art can readily utilize well-known codon usage tables and synthetic methods to provide a suitable coding sequence for any of the peptides of the invention. See, e.g., Sambrook and Russell, Molecular Cloning: A Laboratory Manual, 3rd Ed., 2001, Cold Spring Harbor Laboratory Press; and Ausubel, et al., Current Protocols in Molecular Biology, 1987-2009, John Wiley Interscience.

In other aspects, the present invention provides compositions comprising any one of the peptides described herein or a plurality thereof. As non-limiting examples, the compositions contain a plurality of peptides that bind to maternal antibodies against STIP1 or a plurality of peptides that bind to maternal antibodies against CRMP2. As further non-limiting examples, the compositions contain a plurality of peptides that bind to maternal antibodies against a plurality of antigens, the plurality of antigens being selected from group consisting of: CRMP2 and GDA, CRMP2 and STIP1, LDH B and YBX1, YBX1 and STIP1, CRMP1, CRMP2 and GDA, CRMP1, CRMP2 and STIP1, CRMP1, CRMP2 and YBX1, and LDH A, LDH B, GDA and YBX1. As additional non-limiting examples, the compositions contain one or more combinations of peptides selected from the group consisting of: SEQ ID NOS:20 and 21, SEQ ID NOS:27 and 55, SEQ ID NOS:20 and 55, SEQ ID NOS:45 and 55, SEQ ID NOS:9 and 28, SEQ ID NOS:20 and 32, SEQ ID NOS:27, 38 and 45, SEQ ID NOS:21, 38 and 55, SEQ ID NOS:32, 38, 45, 55, and 60, and SEQ ID NOS:3, 12, 27 and 28. As further non-limiting examples, the compositions comprise peptides corresponding to SEQ ID NOS: 9, 11, 12, 36, 54, 66, 71, or combinations thereof.

B. Mimotopes

In certain aspects, the present invention provides mimotopes which immunologically mimic a peptide epitope described herein (e.g., a peptide that binds to a maternal antibody that binds to a target polypeptide autoantigen selected from LDH A, LDH B, STIP1, GDA, YBX1, CRMP1, and CRMP2). In some embodiments, the mimotope is a peptide sequence which immunologically mimics the peptide epitope and has sequence homology to the antigenic site.

In other embodiments, the mimotope is a peptide sequence which immunologically mimics the peptide epitope and has a three-dimensional conformation, but not sequence homology, that is similar to the antigenic site.

In some embodiments, the mimotope causes an antibody response similar to the one elicited by the peptide epitope. In certain instances, the antibody response of the mimotope corresponds to binding to the same antigenic site on a maternal antibody to which a peptide epitope binds. The ability of the mimotope to act as a molecular mimic to bind to the maternal antibody can be used to block the antibody from binding to its original target antigen (e.g., LDH A, LDH B, STIP1, GDA, YBX1, CRMP1, and CRMP2).

In some embodiments, the mimotope is obtained from phage display libraries through biopanning. Phage display libraries suitable for screening and identifying candidate mimotopes are typically a multiplicity of phages which express random amino acid sequences of less than 100 amino acids in length, less than 75 amino acids, less than 50 amino acids, less than 25 amino acids, and particularly within the range of about 3 to about 25 amino acids at a location which may be bound by an antibody.

In other embodiments, the mimotope is obtained by screening peptide libraries. In some instances, the peptide library is an overlapping peptide library. In other instances, the peptide library is a truncation peptide library, which may be used to identify the shortest amino acid sequence needed for activity. In yet other instances, the mimotope is obtained by alanine scanning, where alanine is used to substitute each residue sequentially to identify specific amino acid residues responsible for a peptide's activity. In further instances, the mimotope is obtained by positional scanning, which identifies an amino acid of interest at a single position and substitutes it with all other natural amino acids one at a time to identify preferred amino acid residues at that position for increasing a peptide's activity. In related instances, the positional scanning may comprise two position combinatorial scanning or three position combinatorial scanning. Additional methods for designing, screening, and determining mimotopes are described in, e.g., U.S. Pat. No. 4,833,092, the disclosure of which is incorporated by reference in its entirety for all purposes.

In further embodiments, the mimotope may comprise a peptide sequence which is structurally more constrained than a linear form of the sequence. An unsubstituted linear peptide such as present free in solution would normally be able to assume a large number of different conformations. In contrast, a peptide which is structurally constrained, perhaps by having one or usually two or more substituents which reduce in number the possible conformations which it can assume, is also within the scope of the present invention.

Substituents such as covalent linkages to further peptide chains or intramolecular linkages will structurally constrain the peptide. For example, the peptide may form part of the primary structure of a larger polypeptide containing the amino acid sequence of the peptide. In certain instances, the peptide comprises a cyclic peptide.

Other substituents include covalent linkages to other moieties such as macromolecular structures including biological and nonbiological structures. Examples of biological structures include, without limitation, carrier proteins. Examples of non-biological structures include lipid vesicles such as liposomes, micelles, lipid nanoparticles, and the like.

In some embodiments, the carrier protein is conjugated to the mimotope. A number of carriers are known for this purpose, including various protein-based carriers such as albumin (e.g., bovine serum albumin (BSA)), keyhole limpet hemocyanin (KLH), ovalbumin (OVA), tetanus toxoid (TT), high-molecular weight proteins (HMP) from nontypeable *Haemophilus influenzae*, diphtheria toxoid, or bacterial outer membrane protein, all of which may be obtained from biochemical or pharmaceutical supply companies or prepared by standard methodology).

In other embodiments, the mimotope is a component of a vaccine. The vaccine may incorporate one or a plurality of mimotopes in which each mimotope is capable of binding to the same or different maternal antibody to block the antibody from binding to its original target antigen (e.g., LDH A, LDH B, STIP1, GDA, YBX1, CRMP1, and CRMP2). The plurality of mimotopes may be conjugated together, for example, using a polylysine to which each mimotope is conjugated.

In particular embodiments, peptide mimotopes are designed using single amino acid substitutions followed by affinity testing for each peptide construct to determine which peptide mimics have the ability to block autism-specific maternal autoantibodies. In certain instances, D-amino acids are used when synthesizing the peptide mimotopes as peptides synthesized from D-amino acids are more resistant to proteolytic digestion and have a longer half-life in vivo. In other instances, peptide mimotopes for each autoantigen are fused to a polyethylene glycol (PEG) scaffold, which leads to the creation of a heteromultimer capable of neutralizing autism-specific maternal autoantibodies. See, e.g., Kessel et al., Chem Med Chem. 4(8):1364-70, 2009.

As peptides on a PEG scaffold are less immunogenic than individual peptides, the mimotope peptides linked to a PEG scaffold are useful as an antibody blocker. The peptide mimotopes may be synthesized with 9-fluorenyl-methoxy-carbonyl-protected amino acid chemistry on appropriate polyethylene glycol (PEG)-PS resin (GenScript Corporation; Piscataway, NJ) by using an automated peptide synthesizer (Pioneer; Applied Biosystems; Foster City, CA). Cleavage of the peptides from the resin and removal of the protecting groups from the side chain may be carried out by using trifluoroacetic acid with scavengers. The crude peptides may be purified by reverse-phase high-performance liquid chromatography using a preparatory C18 column with a gradient of solvent A [95%/5%, $H_2O$ (0.1% trifluoroacetic acid)/acetonitrile] and solvent B (100% acetonitrile). The purity of the peptides is then analyzed by high-performance liquid chromatography using an analytical C18 column. The identity of the synthesized peptide may also be confirmed by matrix-assisted laser desorption ionization/time of flight mass spectrometry. In certain instances, peptide mimotopes may be PEGylated using a strategy that involves the reversible protection of specific residues on the peptides. This procedure is possible for peptides only because they generally contain just a few nucleophilic groups and are more stable than full-length proteins toward the harsh chemical treatments involved in this process. This method involves three steps: (1) protection by suitable reagents of the residues known to be important for the activity and, eventually, the purification of the desired isomers; (2) PEGylation at the level of the lone unprotected, reactive target residue; and (3) removal of all the protecting groups.

To determine if the multimerized peptide mimotopes bind to anti-brain autoantibodies in patient serum, an ELISA assay may be utilized. ELISA assays may also be used to determine if the multimerized peptide mimotopes inhibit the antigen-antibody interaction against the native antigen protein. This may be accomplished by pre-incubating maternal antibody positive plasma with the heteromultimer before performing the ELISA.

An animal model may be used to examine the efficacy, safety, and/or pharmacokinetic properties of the peptide mimotopes in vivo. As a non-limiting example, a mouse model of maternal autoantibody related (MAR) autism may be used. See, e.g., Example 5. MAR autism and control dams (i.e., pregnant female mice) may be randomly assigned to one of two treatment conditions: gestational mimotope treatment or a saline control. Once tolerance has been broken in MAR autism dams, dams assigned to the treatment group may be administered the mimotope peptides via intravenous injection. The efficacy of the mimotopes in vivo may be determined by administration of 200 μg of mimotope to the dam every 24 hours for a total of 4 injections. Reduction of murine autoantibody titer by the peptide mimotope following treatment may be determined using an ELISA assay against the whole target antigen protein. A series of treatment trials may be conducted to determine how many treatments are necessary to reduce/block the murine maternal antibodies for the duration of gestation. Upon determining the ideal treatment regime, dams may be bred to produce offspring for subsequent behavioral analyses.

In particular embodiments, the peptide is a mimotope comprising D-amino acids at some or all of the positions in the amino acid sequence and/or comprising amino acid modifications (e.g., substitutions) at one or more (e.g., at least 1, 2, 3, 4, 5, 6, 7, 8, 9, or 10) positions in the amino acid sequence relative to the amino acid sequence of any one of SEQ ID NOS:1-96.

C. Kits

The present invention also provides kits for the diagnosis or prognosis of whether an offspring such as a fetus or child is at an increased risk of developing an autism spectrum disorder (ASD). Relatedly, the kits also find use for the diagnosis or prognosis of whether a mother or potential mother is at an increased risk of bearing a child who will develop an ASD.

Materials and reagents to carry out these various methods can be provided in kits to facilitate execution of the methods. As used herein, the term "kit" includes a combination of articles that facilitates a process, assay, analysis, or manipulation. In particular, kits comprising the peptides or compositions of the present invention find utility in a wide range of applications including, for example, diagnostics, prognostics, immunotherapy, and the like.

In particular embodiments, the kits comprise any one or a plurality of the peptides described herein (e.g., peptide epitopes and mimotopes thereof) that specifically bind to maternal antibodies against antigenic polypeptides including lactate dehydrogenase A (LDH A), lactate dehydrogenase B (LDH B), stress-induced phosphoprotein 1 (STIP1), guanine deaminase (GDA), Y Box Binding Protein 1 (YBX1), collapsin response mediator protein 1 (CRMP1), and collapsin response mediator protein 2 (CRMP2) and a solid support. In some instances, the kits comprise peptides (e.g., peptide epitopes and mimotopes thereof) corresponding to SEQ ID NOS: 9, 11, 12, 36, 54, 66, 71, and combinations thereof.

In some embodiments, the solid support comprises at least one peptide, e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 peptides. In certain instances, the solid support comprises a peptide selected from the group consisting of an LDH A peptide epitope, an LDH B peptide epitope, a GDA peptide epitope, a STIP1 peptide epitope, a YBX1 peptide epitope, a CRMP1 peptide epitope, a CRMP2 peptide epitope, and combinations thereof. In some embodiments, the solid support comprises one or more peptides having at least about 80%, 85%, 90%, 91%, 92%, 93%, 94%, 95%, 96%, 97%, 98%, 99% or 100% identity with the peptides described herein, e.g., with the amino acid sequence of any one of SEQ ID NOS:1-96. In other embodiments, the solid support comprises one or more peptides having the amino acid sequence set forth in any one of SEQ ID NOS:1-96 or fragments thereof.

In some embodiments, the peptide or plurality of peptides can be immobilized on the solid support. In other embodiments, the solid support is a multiwell plate, an ELISA plate, a microarray, a chip, a bead, a porous strip, or a nitrocellulose filter. The immobilization can be via covalent or non-covalent binding. In some embodiments, the immobilization is through a capture antibody that specifically binds to the one or more peptides. In certain instances, the solid support in the kits are provided prepared with one or more immobilized peptides.

In certain embodiments, the plurality of peptides in the kit comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 different peptides, e.g., selected from SEQ ID NOS: 1-96 and mimotopes thereof. In certain instances, each of the different peptides in the kit binds to the same maternal antibodies, e.g., all of the different peptides bind to maternal antibodies against a single antigen selected from LDH A, LDH B, STIP1, GDA, YBX1, CRMP1, and CRMP2. In certain other instances, each of the different peptides in the kit binds to at least 2, 3, 4, 5, 6, or 7 different maternal antibodies, e.g., the different peptides bind to maternal antibodies against 2, 3, 4, 5, 6, or all 7 of the following antigens: LDH A, LDH B, STIP1, GDA, YBX1, CRMP1, and CRMP2.

In particular embodiments, the plurality of peptides in the kit make up one or more panels, wherein each panel contains a combination of peptides that bind to maternal antibodies against 1, 2, 3, 4, 5, 6, or 7 of the following antigens: LDH A, LDH B, STIP1, GDA, YBX1, CRMP1, and CRMP2. As non-limiting examples, each panel contains a combination of peptides that bind to maternal antibodies against STIP1 or CRMP2. As further non-limiting examples, each panel contains a combination of peptides that bind to maternal antibodies against a plurality of antigens, the plurality of antigens being selected from group consisting of: CRMP2 and GDA, CRMP2 and STIP1, LDH B and YBX1, YBX1 and STIP1, CRMP1, CRMP2 and GDA, CRMP1, CRMP2 and STIP1, CRMP1, CRMP2 and YBX1 and LDH A, LDH B, GDA and YBX1. As additional non-limiting examples, the kits contain one or more combinations of peptides selected from the group consisting of: SEQ ID NOS:20 and 21, SEQ ID NOS:27 and 55, SEQ ID NOS:20 and 55, SEQ ID NOS:45 and 55, SEQ ID NOS:9 and 28, SEQ ID NOS:20 and 32, SEQ ID NOS:27, 38 and 45, SEQ ID NOS:21, 38 and 55, SEQ ID NOS:32, 38, 45, 55, and 60, and SEQ ID NOS:3, 12, 27 and 28.

Kits can contain chemical reagents as well as other components. In addition, the kits of the present invention can include, without limitation, instructions to the kit user, apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, solutions, buffers or other chemical reagents, suitable samples to be used for standardization, normalization, and/or control samples. Kits of the present invention can also be packaged for convenient storage and safe shipping, for example, in a box having a lid.

In some embodiments, the kits also comprise labeled secondary antibodies used to detect the presence of maternal autoantibodies that bind to one or more peptides. The secondary antibodies bind to the constant or "C" regions of different classes or isotypes of immunoglobulins IgM, IgD, IgG, IgA, and IgE. Usually, a secondary antibody against an IgG constant region is included in the kits, such as, e.g., secondary antibodies against one of the IgG subclasses (e.g., IgG1, IgG2, IgG3, and IgG4). Secondary antibodies can be labeled with any directly or indirectly detectable moiety, including a fluorophore (e.g., fluoroscein, phycoerythrin, quantum dot, Luminex bead, fluorescent bead), an enzyme (e.g., peroxidase, alkaline phosphatase), a radioisotope (e.g., $^3$H, $^{32}$P, $^{125}$I) or a chemiluminescent moiety. Labeling signals can be amplified using a complex of biotin and a biotin binding moiety (e.g., avidin, streptavidin, neutravidin). Fluorescently labeled anti-human IgG antibodies are commercially available from Molecular Probes, Eugene, OR. Enzyme-labeled anti-human IgG antibodies are commercially available from Sigma-Aldrich, St. Louis, MO and Chemicon, Temecula, CA.

The kits may further comprise instructions for contacting the solid support with a biological sample from a mother or potential mother, and for correlating the presence of maternal antibodies or levels of maternal antibodies above a threshold level with an increased probability that a fetus or child of the mother or potential mother will develop an ASD.

In some embodiments, the kits also contain negative and positive control samples for detection of maternal antibodies. In some instances, the negative control samples are obtained from mothers who have TD children. In other instances, the negative and/or positive control samples are reactive to 1, 2, 3, 4, 5, 6, or all 7 of the following full-length antigens: LDH A, LDH B, STIP1, GDA, YBX1, CRMP1, and CRMP2. In yet other instances, the negative and/or positive control samples do not react to any of the full-length antigens LDH A, LDH B, STIP1, GDA, YBX1, CRMP1, or CRMP2. In some embodiments, the kits contain samples for the preparation of a titrated curve of maternal antibodies in a sample, to assist in the evaluation of quantified levels of antibodies in a test biological sample. In particular embodiments, the kit comprises one or more peptides described in SEQ ID NOS:1-96, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 of the peptides described in SEQ ID NOS:1-96.

The kits find use for providing a diagnosis or prognosis to any women of childbearing age. A diagnosis or prognosis can be determined before, during, or after pregnancy. Detection of maternal antibodies can be made in one or more of the first, second, and/or third trimesters of pregnancy. In some embodiments, detection of maternal antibodies is performed on a biological sample from a woman carrying a fetus whose brain has begun to develop, e.g., after about 12 weeks of gestation. In some embodiments, the presence or absence of maternal antibodies or the quantified levels of maternal antibodies are evaluated one or more times postpartum, e.g., in the first four weeks after birth and/or while the mother is breastfeeding the child. In some embodiments, the presence of maternal antibodies or the quantified levels of maternal antibodies are evaluated one or more times before pregnancy or in any woman who is not pregnant.

D. Patients Subject to Diagnosis or Treatment

The methods of the present invention can be performed on any mammal, for example, a human, a non-human primate, a laboratory mammal (e.g., a mouse, a rat, a rabbit, a hamster), a domestic mammal (e.g., a cat, a dog), or an agricultural mammal (e.g., bovine, ovine, porcine, equine). In some embodiments, the patient is a woman and a human.

Any woman capable of bearing a child can benefit from the methods of the present invention. The child may or may not be conceived, i.e., the woman can be but need not be pregnant. In some embodiments, the woman has a child who is a neonate. In some embodiments, the woman is of childbearing age, i.e., she has begun to menstruate and has not reached menopause.

In some embodiments, the diagnostic and prevention and/or treatment methods of the present invention are performed on a woman carrying a fetus (i.e., who is pregnant). The methods can be performed at any time during pregnancy. In some embodiments, the methods are performed on a woman carrying a fetus whose brain has begun to develop. For example, the fetus may at be at about 12 weeks of gestation or later. In some embodiments, the woman subject to treatment or diagnosis is in the second or third trimester of pregnancy. In some embodiments, the woman subject to treatment or diagnosis is in the first trimester of pregnancy. In some embodiments, the woman is post-partum, e.g., within 6 month of giving birth. In some embodiments, the woman is post-partum and breastfeeding.

Women who will benefit from the present methods may but need not have a familial history of an ASD or an autoimmune disease. For example, the woman may have an ASD or have a family member (e.g., a parent, a child, a grandparent) with an ASD. In some embodiments, the woman suffers from an autoimmune disease or has a family member (e.g., a parent, a child, a grandparent) who suffers from an autoimmune disease.

In some embodiments, the methods of the present invention comprise the step of determining that the diagnosis or treatment is appropriate for the patient, e.g., based on prior medical history or familial medical history or pregnancy status or any other relevant criteria.

E. Methods of Determining Risk of Developing Autism Spectrum Disorder

In certain aspects, the present invention provides methods for determining the likelihood or risk that a fetus or child will develop an autism spectrum disorder (ASD) comprising identifying in a biological sample from the mother or potential mother of the fetus or child the presence of maternal autoantibodies that bind to 1, 2, 3, 4, 5, 6, or 7 of the target polypeptide antigens described herein, e.g., lactate dehydrogenase A (LDH A), lactate dehydrogenase B (LDH B), stress-induced phosphoprotein 1 (STIP1), guanine deaminase (GDA), Y Box Binding Protein 1 (YBX1), collapsin response mediator protein 1 (CRMP1), and collapsin response mediator protein 2 (CRMP2). The methods comprise detecting in the biological sample the presence or absence of maternal autoantibodies that bind to any one of the peptides described herein or a plurality thereof, wherein the presence of maternal autoantibodies that bind to the peptide or plurality thereof indicates an increased likelihood or risk that the fetus or child will develop an ASD.

With respect to the biological sample taken from the mother or potential mother, any fluid sample containing antibodies can be used. For example, the biological sample may be blood, serum, plasma, amniotic fluid, urine, breast milk or saliva. Of course, one or more different bodily fluids can be evaluated for antibodies that specifically bind to the one or more peptides.

In particular embodiments, the biological sample is evaluated for the presence of maternal antibodies that specifically bind to at least one or more of the peptides described herein (e.g., SEQ ID NOS:1-96), e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 of the peptides set forth in SEQ ID NOS:1-96. In some instances, the biological sample is evaluated for the presence of maternal antibodies that specifically bind to peptides corresponding to SEQ ID NOS: 9, 11, 12, 36, 54, 66, 71, and combinations thereof. In some embodiments, the presence of maternal antibodies that specifically bind one or more of the target polypeptide autoantigens, e.g., 1, 2, 3, 4, 5, 6, or 7 target polypeptide autoantigens, including LDH A, LDH B, STIP1, GDA, YBX1, CRMP1, CRMP2 or any combination thereof, is detected in the sample using one or more of the peptides described herein (e.g., SEQ ID NOS: 1-96). As a non-limiting example, one or more peptides, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 different peptides as set forth in SEQ ID NOS:1-96 can be used to detect the presence or absence of maternal antibodies in the sample.

In certain instances, each of the different peptides binds to the same maternal antibodies, e.g., all of the different peptides bind to maternal antibodies against a single polypeptide autoantigen selected from LDH A, LDH B, STIP1, GDA, YBX1, CRMP1, and CRMP2. In certain other instances, each of the different peptides binds to at least 2, 3, 4, 5, 6, or 7 different maternal antibodies, e.g., the different peptides bind to maternal antibodies against 2, 3, 4, 5, 6, or all 7 of the following polypeptide autoantigens: LDH A, LDH B, STIP1, GDA, YBX1, CRMP1, and CRMP2.

In some embodiments, the presence of maternal antibodies against 1 polypeptide autoantigen, e.g., any single autoantigen selected from LDH A, LDH B, STIP1, GDA, YBX1, CRMP1, and CRMP2, is detected. As non-limiting examples, panels comprising a plurality of peptides that bind to maternal antibodies against combinations of STIP1 or CRMP2 are used for detection. As additional non-limiting examples, the panels contain combinations of peptides selected from the group consisting of: SEQ ID NOS:20 and 21 and SEQ ID NOS:45 and 55.

In some embodiments, the presence of maternal antibodies against 2 different polypeptide autoantigens, e.g., any combination of autoantigens selected from LDH A and LDH B, LDH A and STIP1, LDH A and GDA, LDH A and YBX1, LDH A and CRMP1, LDH A and CRMP2, LDH B and STIP1, LDH B and GDA, LDH B and YBX1, LDH B and CRMP1, LDH B and CRMP2, STIP1 and GDA, STIP1 and YBX1, STIP1 and CRMP1, STIP1 and CRMP2, GDA and YBX1, GDA and CRMP1, GDA and CRMP2, YBX1 and CRMP1, YBX1 and CRMP2, or CRMP1 and CRMP2, is detected. As non-limiting examples, panels comprising a plurality of peptides that bind to maternal antibodies against combinations of CRMP2 and GDA, CRMP2 and STIP1, LDH B and YBX1, or YBX1 and STIP1 are used for detection. As additional non-limiting examples, the panels contain combinations of peptides selected from the group consisting of: SEQ ID NOS:27 and 55, SEQ ID NOS:20 and 55, SEQ ID NOS:9 and 28, and SEQ ID NOS:20 and 32.

In some embodiments, the presence of maternal antibodies against 3 different polypeptide autoantigens, e.g., a combination of any 3 autoantigens selected from LDH A, LDH B, STIP1, GDA, YBX1, CRMP1, and CRMP2, is detected. As non-limiting examples, panels comprising a plurality of peptides that bind to maternal antibodies against combinations of CRMP1, CRMP2 and GDA, CRMP1, CRMP2 and STIP1, or CRMP1, CRMP2 and YBX1 are used for detection. As additional non-limiting examples, the panels contain combinations of peptides selected from the group consisting of: SEQ ID NOS:27, 38 and 45, SEQ ID NOS:21, 38 and 55, and SEQ ID NOS:32, 38, 45, 55, and 60.

In some embodiments, the presence of maternal antibodies against 4 different polypeptide autoantigens, e.g., a combination of any 4 autoantigens selected from LDH A, LDH B, STIP1, GDA, YBX1, CRMP1, and CRMP2, is detected. As a non-limiting example, a panel comprising a plurality of peptides that bind to maternal antibodies against a combination of LDH A, LDH B, GDA, and YBX1 is used for detection. As an additional non-limiting example, the panel contains a combination of peptides consisting of SEQ ID NOS:3, 12, 27, and 28.

In some embodiments, the presence of maternal antibodies against 5 different polypeptide autoantigens, e.g., a combination of any 5 autoantigens selected from LDH A, LDH B, STIP1, GDA, YBX1, CRMP1, and CRMP2, is detected.

In some embodiments, the presence of maternal antibodies against 6 different polypeptide autoantigens, e.g., a combination of any 6 autoantigens selected from LDH A, LDH B, STIP1, GDA, YBX1, CRMP1, and CRMP2, is detected.

In some embodiments, the presence of maternal antibodies against all 7 of the following polypeptide autoantigens is detected: LDH A, LDH B, STIP1, GDA, YBX1, CRMP1, and CRMP2.

In certain instances, the presence of maternal antibodies against LDH A can be detected using 1, 2, 3, 4, 5, 6, 7, 8, 9, or 10 peptides set forth in SEQ ID NOS:1-7 and 62-64 or antigenic fragments thereof. The presence of antibodies against LDH B can be detected using 1, 2, 3, 4, 5, 6, 7, 8, 9, 10, 11, 12, 13, 14, 15, 16, 17, 18, 19, or 20 peptides as set forth in SEQ ID NOS:8-19 and 65-72 or antigenic fragments thereof. The presence of antibodies against STIP1 can be detected using 1, 2, 3, 4, 5, 6, 7, or 8 peptides set forth in SEQ ID NOS:20-23 and 73-76 or antigenic fragments thereof. In some instances, the presence of maternal antibodies against GDA can be detected using 1, 2, 3, 4, 5, 6, or 7 peptides set forth in SEQ ID NOS:24-27 and 77-79 or antigenic fragments thereof. In other instances, the presence of maternal antibodies against YBX1 can be detected using 1, 2, 3, 4, 5, 6, 7, 8, 9, 10, 11, or 12 peptides set forth in SEQ ID NOS:28-25 and 80-83 or antigenic fragments thereof. Maternal antibodies against CRMP1 can be detected using 1, 2, 3, 4, 5, 6, 7, 8, 9, 10, 11, 12, 13, or 14 peptides set forth in SEQ ID NOS:36-44 and 84-88 or antigenic fragments thereof. In some instances, the presence of maternal antibodies against CRMP2 can be detected using 1, 2, 3, 4, 5, 6, 7, 8, 9, 10, 11, 12, 13, 14, 15, 16, 17, 18, 19, 20, 21, 22, 23, 24, or 25 peptides set forth in SEQ ID NOS:45-61 and 89-96 or antigenic fragments thereof.

In some embodiments, detection of the presence of maternal antibodies (versus the absence of detection of maternal antibodies) indicates an increased probability that the fetus or child has or will develop an ASD.

In some embodiments, the level or titer of the maternal antibodies in the biological sample is compared to a threshold level or titer. A level or titer of the antibodies in the biological sample that is greater than the threshold level or titer indicates an increased probability that the fetus or child has or will develop an ASD. Likewise, a level or titer of the antibodies in the biological sample that is less than the threshold level or titer does not indicate an increased probability (i.e., indicates no increased probability) that the fetus or child has or will develop an ASD. The threshold level or titer for maternal antibodies in a particular biological fluid can be determined by evaluating levels of maternal antibodies in populations of pregnant women and comparing the antibody levels or titer in the biological fluid of the mother when the child developed an ASD and to the antibody levels or titer in the biological fluid of the mother when the child did not develop an ASD. The threshold levels or titer can also be determined at different time points during pregnancy, e.g., every four weeks, every two weeks or every week during gestation of the fetus. Threshold antibody levels or titer can also be measured after the child is born, e.g., in the first four weeks after birth and/or while the mother is breastfeeding the child.

The presence of the maternal antibodies against the target polypeptide autoantigens described herein or the quantified levels of the maternal antibodies against the target polypeptide autoantigens can be determined before, during, or after pregnancy. When determined during pregnancy, detection of the maternal antibodies can be performed one, two, three, four or more times, as appropriate, at any time during the course of pregnancy. For example, detection of the maternal antibodies can be made in one or more of the first, second and/or third trimesters of pregnancy. In some embodiments, detection of the maternal antibodies is performed on a biological sample from a woman carrying a fetus whose brain has begun to develop, e.g., after about 12 weeks of gestation. In some embodiments, the presence or absence of maternal antibodies or the quantified levels of maternal antibodies are evaluated one or more times post-partum, e.g., in the first four weeks after birth and/or while the mother is breastfeeding the child. In some embodiments, the presence or absence of the maternal antibodies or the quantified levels of the maternal antibodies are evaluated one or more times before pregnancy or in any women who is not pregnant.

The presence of the maternal antibodies may be determined once or more than once, as needed or desired. In some embodiments, the presence or absence of maternal antibodies or the quantified levels of maternal antibodies are evaluated every four weeks, every two weeks or every week during pregnancy, or more or less often, as appropriate.

In some embodiments, presence of the maternal antibodies is made without comparing the test sample (i.e., a biological sample from the mother or potential mother) to a control sample. In other embodiments, the test sample is compared to a control. The control can be from the same individual at a different time point. For example, the test sample can be taken during pregnancy, and the control sample can be taken from the same individual before pregnancy. In some instances, the test sample will be taken relatively later in pregnancy term and the control sample will be taken from the same individual earlier in pregnancy term. In this case, if the level of maternal antibodies is greater in the test sample than in the control sample, then the fetus or child is at an increased risk of developing an ASD. If several samples are evaluated over the course of a pregnancy, increased levels or titers of maternal antibodies over the term of the pregnancy indicate an increased risk that the fetus or child will develop an ASD. Similarly, absent or decreased levels or titers of the maternal antibodies over the term of the pregnancy indicate a low or reduced risk that the fetus or child will develop an ASD.

The control can also be from a different individual with a known status for the presence of the maternal antibodies. The control can also be a calculated value from a population of individuals with a known status for the presence of maternal antibodies. The control may be a positive control or a negative control. In some instances, the negative control is obtained from a mother who has a TD child. In other instances, the negative and/or positive control sample reacts to 1, 2, 3, 4, 5, 6, or all 7 of the following full-length antigens: LDH A, LDH B, STIP1, GDA, YBX1, CRMP1, and CRMP2. In yet other instances, the negative and/or positive control sample does not react to any of the full-length antigens LDH A, LDH B, STIP1, GDA, YBX1, CRMP1, or CRMP2.

In some embodiments, the control is a negative control from another individual or a population of individuals. If the known status of the control sample is negative for the antibodies, then a higher level of maternal antibodies in the test sample than in the negative control sample indicates that the fetus or child is at an increased risk of developing an ASD. A similar level of maternal antibodies in the test sample to the negative control sample indicates that the fetus or child is not at an increased risk, i.e., has a low or reduced risk, of developing an ASD.

In some embodiments, the control is a positive control from another individual or a population of individuals, or the control reflects a predetermined threshold level of antibodies. If the known status of the control sample is positive for antibodies, then a similar or higher level of maternal antibodies in the test sample than in the positive control sample indicates that the fetus or child is at an increased risk of developing an ASD. A lower level of maternal antibodies in the test sample to the control sample indicates that the fetus or child is not at an increased risk or has a low or reduced risk of developing an ASD.

The differences between the control sample or value and the test sample need only be sufficient to be detected. In some embodiments, an increased level of maternal antibodies in the test sample, and hence an increased risk of an ASD, is determined when the antibody levels are at least, e.g., 10%, 25%, 50%, 1-fold, 2-fold, 3-fold, 4-fold, or more in comparison to a negative or a prior-measured control.

For the purposes of diagnosing an increased likelihood that a fetus or child will develop an ASD, the presence of maternal antibodies against any subtype, isoform or isozyme of one or more target polypeptide autoantigens (e.g., LDH A, LDH B, GDA, STIP1, YBX1, CRMP1, and/or CRMP2) can be determined.

The maternal antibodies can be detected using any method known in the art. Exemplary methods include, without limitation, Western Blot, dot Blot, enzyme-linked immunosorbent assay (ELISA), radioimmunoassay (MA), electrochemiluminescence, and multiplex bead assays (e.g., using Luminex or fluorescent microbeads).

The peptides can be antigenic fragments of the target polypeptide autoantigens. The peptides can be derived from known antigenic epitopes of the autoantigens, with one or more amino acids substituted, deleted, added, or otherwise modified. The peptides can be purified or substantially purified from a natural source, or recombinantly or synthetically produced.

In some embodiments, the peptides used to detect maternal antibodies can be immobilized on a solid support. The solid support can be, for example, a multiwell plate, a microarray, a chip, a bead, a porous strip, or a nitrocellulose filter. The immobilization can be via covalent or non-covalent binding. In some embodiments, the immobilization is through a capture antibody that specifically binds to the target epitope.

For detection of maternal antibodies, a sample can be incubated with one or more of the peptides described herein under conditions (e.g., time, temperature, concentration of sample) sufficient to allow specific binding of any antibodies that specifically bind to one or more target antigens present in the sample. The one or more peptides can be bound to a solid support. For example, the one or more peptides can be exposed to a sample for about 0.5, 1.0, 1.5, 2.0, 2.5, 3.0 hours, or overnight, about 8, 10, 12, 14, or 16 hours. However, incubation time can be more or less depending on, e.g., the composition of the one or more peptides, the composition of the one or more target antigens, the dilution of the sample, and the temperature for incubation. Incubations using less diluted samples and higher temperatures can be carried out for shorter periods of time. Incubations are usually carried out at room temperature (about 25° C.) or at biological temperature (about 37° C.), and can be carried out in a refrigerator (about 4° C.). Washing to remove unbound sample before addition of a secondary antibody is carried according to known immunoassay methods.

Labeled secondary antibodies are generally used to detect antibodies in a sample that have bound to one or more of the peptides described herein. Secondary antibodies bind to the constant or "C" regions of different classes or isotypes of immunoglobulins IgM, IgD, IgG, IgA, and IgE. Usually, a secondary antibody against an IgG constant region is used in the present methods. Secondary antibodies against the IgG subclasses, for example, IgG1, IgG2, IgG3, and IgG4, also find use in the present methods. Secondary antibodies can be labeled with any directly or indirectly detectable moiety, including a fluorophore (e.g., fluoroscein, phycoerythrin, quantum dot, Luminex bead, fluorescent bead), an enzyme (e.g., peroxidase, alkaline phosphatase), a radioisotope (e.g., $^3$H $^{32}$P, $^{125}$I) or a chemiluminescent moiety. Labeling signals can be amplified using a complex of biotin and a biotin binding moiety (e.g., avidin, streptavidin, neutravidin). Fluorescently labeled anti-human IgG antibodies are commercially available from Molecular Probes, Eugene, OR. Enzyme-labeled anti-human IgG antibodies are commercially available from Sigma-Aldrich, St. Louis, MO and Chemicon, Temecula, CA.

The method of detection of the presence or absence, or differential presence, of autoantibodies in a sample will correspond with the choice of label of the secondary antibody. For example, if one or more of the peptides described herein are transferred onto a membrane substrate suitable for immunoblotting, the detectable signals (i.e., blots) can be quantified using a digital imager if enzymatic labeling is used or an x-ray film developer if radioisotope labeling is used. In another example, if one or more of the peptides described herein are transferred to a multi-well plate, the detectable signals can be quantified using an automated plate reader capable of detecting and quantifying fluorescent, chemiluminescent, and/or colorimetric signals. Such methods of detection are well known in the art.

General immunoassay techniques are well known in the art. Guidance for optimization of parameters can be found in, for example, Wu, Quantitative Immunoassay: A Practical Guide for Assay Establishment, Troubleshooting, and Clinical Application, 2000, AACC Press; Principles and Practice of Immunoassay, Price and Newman, eds., 1997, Groves Dictionaries, Inc.; The Immunoassay Handbook, Wild, ed., 2005, Elsevier Science Ltd.; Ghindilis, Pavlov and Atanassov, Immunoassay Methods and Protocols, 2003, Humana Press; Harlow and Lane, Using Antibodies: A Laboratory Manual, 1998, Cold Spring Harbor Laboratory Press; and Immunoassay Automation: An Updated Guide to Systems, Chan, ed., 1996, Academic Press.

In certain embodiments, the presence or increased presence of maternal antibodies is indicated by a detectable signal (e.g., a blot, fluorescence, chemiluminescence, color, radioactivity) in an immunoassay, where the biological sample from the mother or potential mother is contacted with one or more of the peptides described herein. This detectable signal can be compared to the signal from a control sample or to a threshold value. In some embodiments, increased presence is detected, and an increased risk of ASD is indicated, when the detectable signal of maternal antibodies in the test sample is at least about 10%, 20%, 30%, 50%, 75% greater in comparison to the signal of maternal antibodies in the control sample or the predetermined threshold value. In some embodiments, an increased presence is detected, and an increased risk of ASD is indicated, when the detectable signal of maternal antibodies in the test sample is at least about 1-fold, 2-fold, 3-fold, 4-fold or more, greater in comparison to the signal of maternal antibodies in the control sample or the predetermined threshold value.

In some embodiments, the results of the maternal antibody determinations are recorded in a tangible medium. For example, the results of the present diagnostic assays (e.g., the observation of the presence or increased presence of maternal antibodies) and the diagnosis of whether or not an increased risk of ASD is determined can be recorded, e.g., on paper or on electronic media (e.g., audio tape, a computer disk, a CD, a flash drive, etc.).

In other embodiments, the methods further comprise the step of providing the diagnosis to the patient (i.e., the mother or potential mother) of whether or not there is an increased risk that a fetus or child of the patient will develop an ASD based on the results of the maternal antibody determinations.

F. Methods of Reducing Risk by Administering Peptide Epitopes

In certain aspects, the present invention provides methods for preventing and/or reducing the risk of developing an autism spectrum disorder (ASD) in a fetus or child by administering in vivo to the mother or potential mother a blocking agent or plurality of blocking agents selected from an LDH A peptide epitope, an LDH B peptide epitope, a STIP1 peptide epitope, a GDA peptide epitope, a YBX1 peptide epitope, a CRMP1 peptide epitope, a CRMP2 peptide epitope, and any combination thereof or a mimotope thereof that specifically binds to maternal autoantibodies associated with ASD. The blocking agent can prevent the maternal antibodies from specifically binding the endogenous polypeptide autoantigen present in the fetus or child.

In some embodiments, the methods include administering to the mother or potential mother at least one blocking agent comprising at least one or more of the peptides described herein (e.g., SEQ ID NOS:1-96) or mimotopes thereof, e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 of the peptides set forth in SEQ ID NOS:1-96 or mimotopes thereof. In certain instances, the blocking agent comprises peptides or mimotopes thereof corresponding to SEQ ID NOS: 9, 11, 12, 36, 54, 66, 71, and combinations thereof. In some instances, the blocking agent specifically binds to a maternal antibody that recognizes the antigen LDH A, LDH B, STIP1, GDA, YBX1, CRMP1, or CRMP2. In some embodiments, the methods include administering to the mother or potential mother one or more peptides or mimotopes thereof that are recognized by 1, 2, 3, 4, 5, 6 or 7 different maternal antibodies. In certain instances, each of the different peptides or mimotopes binds to the same maternal antibodies, e.g., all of the different peptides or mimotopes bind to maternal antibodies against a single antigen selected from LDH A, LDH B, STIP1, GDA, YBX1, CRMP1, and CRMP2. In certain other instances, each of the different peptides or mimotopes binds to at least 2, 3, 4, 5, 6, or 7 different maternal antibodies, e.g., the different peptides or mimotopes bind to maternal antibodies against 2, 3, 4, 5, 6, or all 7 of the following antigens: LDH A, LDH B, STIP1, GDA, YBX1, CRMP1, and CRMP2.

As non-limiting examples, the blocking agent comprises a combination of peptides that bind to maternal antibodies against STIP1 or CRMP2. As further non-limiting examples, the blocking agent comprises a combination of peptides that bind to maternal antibodies against a plurality of antigens, the plurality of antigens being selected from group consisting of: CRMP2 and GDA, CRMP2 and STIP1, LDH B and YBX1, YBX1 and STIP1, CRMP1, CRMP2 and GDA, CRMP1, CRMP2 and STIP1, CRMP1, CRMP2 and YBX1, and LDH A, LDH B, GDA and YBX1. As additional non-limiting examples, the blocking agent comprises one or more combinations of peptides selected from the group consisting of: SEQ ID NOS:20 and 21, SEQ ID NOS:27 and 55, SEQ ID NOS:20 and 55, SEQ ID NOS:45 and 55, SEQ ID NOS:9 and 28, SEQ ID NOS:20 and 32, SEQ ID NOS:27, 38 and 45, SEQ ID NOS:21, 38 and 55, SEQ ID NOS:32, 38, 45, 55, and 60, and SEQ ID NOS:3, 12, 27 and 28.

The prevention and/or treatment methods of the present invention using a blocking agent or plurality of blocking agents can be provided to a woman before, during, or after pregnancy. In some embodiments, the blocking agent(s) can be administered one, two, three, four or more times, as appropriate, at any time during the course of pregnancy. For example, the blocking agent(s) can be administered in one or more of the first, second and/or third trimesters of pregnancy. In some embodiments, the blocking agent(s) are administered to a woman carrying a fetus whose brain has begun to develop, e.g., after about 12 weeks of gestation. In some embodiments, the blocking agent(s) are administered one or more times post-partum, e.g., in the first four weeks after birth and/or while the mother is breastfeeding the child. In some embodiments, the blocking agent(s) are administered one or more times before pregnancy, for example, in a woman who has tested positive for maternal antibodies and who is trying to become pregnant.

In some embodiments, a plurality of agents comprising two or more peptides or mimotopes thereof are administered. The plurality of agents can be administered separately or together. The plurality of agents can be a pool of individual peptides or mimotopes. In some embodiments, two or more peptides or mimotopes having different epitopes are chemically linked. The multiple antigenic epitopes can be from the same or different antigenic polypeptides. Chemical linkage in this case may be by direct linking of the peptides or linkage through the use of a chemical scaffold or linker. In some embodiments, two or more peptides or mimotopes having different peptide epitopes are fused together. The peptide epitope fusions can be expressed recombinantly or chemically synthesized.

In some embodiments, the methods further comprise the step of administering to the mother or potential mother a therapeutic or preventative regime of one or more blocking agents (e.g., one or more of the peptides of SEQ ID NOS:1-96 or mimotopes thereof) to reduce, inhibit, or prevent the binding of maternal autoantibodies to 1, 2, 3, 4, 5, 6, or 7 target polypeptide antigens described herein (e.g., selected from LDH A, LDH B, STIP1, GDA, YBX1, CRMP1, and CRMP2).

In some embodiments, one or more blocking agents is administered to reduce, inhibit, or prevent the binding of maternal antibodies against 1 polypeptide autoantigen selected from LDH A, LDH B, STIP1, GDA, YBX1, CRMP1, and CRMP2.

In some embodiments, one or more blocking agents are administered to reduce, inhibit, or prevent the binding of maternal antibodies against 2 different polypeptide autoantigens, e.g., any combination of antigens selected from LDH A and LDH B, LDH A and STIP1, LDH A and GDA, LDH A and YBX1, LDH A and CRMP1, LDH A and CRMP2, LDH B and STIP1, LDH B and GDA, LDH B and YBX1, LDH B and CRMP1, LDH B and CRMP2, STIP1 and GDA, STIP1 and YBX1, STIP1 and CRMP1, STIP1 and CRMP2, GDA and YBX1, GDA and CRMP1, GDA and CRMP2, YBX1 and CRMP1, YBX1 and CRMP2, and CRMP1 and CRMP2.

In some embodiments, one or more blocking agents are administered to reduce, inhibit, or prevent the binding of maternal antibodies against 3 different polypeptide autoantigens, e.g., a combination any 3 antigens selected from LDH A, LDH B, STIP1, GDA, YBX1, CRMP1, and CRMP2.

In some embodiments, one or more blocking agents are administered to reduce, inhibit, or prevent the binding of maternal antibodies against 4 different polypeptide autoantigens, e.g., a combination any 4 antigens selected from LDH A, LDH B, STIP1, GDA, YBX1, CRMP1, and CRMP2.

In some embodiments, one or more blocking agents are administered to reduce, inhibit, or prevent the binding of maternal antibodies against 5 different polypeptide autoantigens, e.g., a combination any 5 antigens selected from LDH A, LDH B, STIP1, GDA, YBX1, CRMP1, and CRMP2.

In some embodiments, one or more blocking agents are administered to reduce, inhibit, or prevent the binding of maternal antibodies against 6 different polypeptide autoantigens, e.g., a combination any 6 antigens selected from LDH A, LDH B, STIP1, GDA, YBX1, CRMP1, and CRMP2.

In some embodiments, one or more blocking agents are administered to reduce, inhibit, or prevent the binding of maternal antibodies against all 7 different of the following polypeptide autoantigens: LDH A, LDH B, STIP1, GDA, YBX1, CRMP1, and CRMP2.

In certain instances, the administered blocking agent or plurality of blocking agents that reduce, inhibit, or prevent the binding of maternal antibodies to an LDH A polypeptide comprises 1, 2, 3, 4, 5, 6, 7, 8, 9, or 10 of the peptides set forth in SEQ ID NOS:1-7 and 62-64 or antigenic fragments or mimotopes thereof. In other instances, the administered blocking agent or plurality of blocking agents that reduce, inhibit, or prevent the binding of maternal antibodies to an LDH B polypeptide comprises 1, 2, 3, 4, 5, 6, 7, 8, 9, 10, 11, 12, 13, 14, 15, 16, 17, 18, 19, or 20 of the peptides as set forth in SEQ ID NOS:8-19 and 65-72 or antigenic fragments or mimotopes thereof. In yet other instances, the administered blocking agent or plurality of blocking agents that reduce, inhibit, or prevent the binding of maternal antibodies to a STIP1 polypeptide comprises 1, 2, 3, 4, 5, 6, 7, or 8 of the peptides set forth in SEQ ID NOS:20-23 and 73-76 or antigenic fragments or mimotopes thereof. In further instances, the administered blocking agent or plurality of blocking agents that reduce, inhibit, or prevent the binding of maternal antibodies to a GDA polypeptide comprises 1, 2, 3, 4, 5, 6, or 7 of the peptides set forth in SEQ ID NOS:24-27 and 77-79 or antigenic fragments or mimotopes thereof. In other instances, the administered blocking agent or plurality of blocking agents that reduce, inhibit, or prevent the binding of maternal antibodies to a YBX1 polypeptide comprises 1, 2, 3, 4, 5, 6, 7, 8, 9, 10, 11, or 12 of the peptides set forth in SEQ ID NOS:28-35 and 80-83 or antigenic fragments or mimotopes thereof. In yet other instances, the administered blocking agent or plurality of blocking agents that reduce, inhibit, or prevent the binding of maternal antibodies to a CRMP1 polypeptide comprises 1, 2, 3, 4, 5, 6, 7, 8, 9, 10, 11, 12, 13, or 14 of the peptides set forth in SEQ ID NOS:36-44 and 84-88 or antigenic fragments or mimotopes thereof. In further instances, the administered blocking agent or plurality of blocking agents that reduce, inhibit, or prevent the binding of maternal antibodies to a CRMP2 polypeptide comprises 1, 2, 3, 4, 5, 6, 7, 8, 9, 10, 11, 12, 13, 14, 15, 16, 17, 18, 19, 20, 21, 22, 23, 24, or 25 of the peptides set forth in SEQ ID NOS:45-61 and 89-96 or antigenic fragments or mimotopes thereof.

The administered blocking agents may contain modifications to reduce or minimize their immunogenicity. Modifications to amino acids in the peptides or mimotopes include, but are not limited to, an amide moiety or a pyroglutamyl residue or the addition of polyethylene glycol chains (PEGylation). These modifications may contribute to decreasing the propensity to form R-sheet conformation or may contribute to peptide stability, solubility and decreased immunogenicity. In some instances, a more stable, soluble and less immunogenic peptide is desirable. Many peptides modified at the C-terminus with a $CONH_2$ (amide) group appear to be resistant to attack by carboxypeptidases and many peptides having a pyroglutamyl residue at the N-terminus are more resistant to attack by broad specificity aminopeptidases. PEGylated peptides have been shown to have increased plasma half-lives and decreased immunogenicity as compared with non-modified peptides. Furthermore, sequence analysis of the blocking agents will allow the minimization of known T-cell epitopes through conservative modifications. Also included as peptides of the present invention are cyclic peptides that are resistant to attack by both carboxypeptidases and aminopeptidases. Additionally, oral administration of the blocking agent may aid in minimizing immunogenicity.

In some embodiments, the prevention and/or treatment methods include the step of first determining the presence or increased presence of maternal antibodies that bind to one or more target polypeptide autoantigens in the mother or potential mother using the detection methods described herein. A woman who tests positive or at a level above the threshold level for the presence of maternal antibodies is a candidate to receive a blocking agent(s) that specifically binds to the maternal antibodies. A woman who tests negative or at a level below the threshold level for the presence of maternal antibodies need not receive a blocking agent(s) that specifically binds to the maternal antibodies.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein. Generally, an efficacious or effective amount of one or more maternal antibody blocking agents is determined by first administering a low dose or small amount of a blocking agent and then incrementally increasing the administered dose or dosages, and/ or adding a second blocking agent(s) as needed, until a desired effect of, e.g., eliminating or reducing the presence of unbound or free maternal antibodies below a predetermined threshold level, is observed in the treated subject, with minimal or no toxic or undesirable side-effects. Applicable methods for determining an appropriate dose and dosing schedule for administration of a pharmaceutical composition of the present invention is described, for example, in Goodman and Gilman's The Pharmacological Basis of Therapeutics, 11th Ed., Brunton, et al., Eds., McGraw-Hill (2006), and in Remington: The Science and Practice of Pharmacy, 21st Ed., University of the Sciences in Philadelphia (USIP), 2005, Lippincott, Williams and Wilkins.

Dosage amount and interval can be adjusted individually to provide plasma or tissue levels of the blocking agent(s) sufficient to maintain a therapeutic effect. Single or multiple administrations of the compositions comprising an effective amount of one or more blocking agents can be carried out with dose levels and pattern selected by the treating physician. The dose and administration schedule can be determined and adjusted, e.g., based on the levels of maternal antibodies in the mother or potential mother, which can be monitored throughout the course of treatment according to methods commonly practiced by clinicians or those described herein. In some embodiments, therapeutic levels will be achieved by administering single daily doses. In other embodiments, the dosing schedule can include multiple daily dose schedules. In still other embodiments, dosing every other day, semi-weekly, or weekly are included in the invention.

For example, the blocking agent(s) can be administered monthly, bi-weekly, weekly or daily, as needed. In some embodiments, the levels of maternal antibodies in the mother or potential mother are monitored and the blocking agent(s) are administered if maternal antibodies are present or are present at levels above a predetermined threshold level. The blocking agent(s) can be administered for a time period of about 1, 2, 3, 4, 5, 10, 12, 15, 20, 24, 30, 32, 36 weeks, or longer or shorter, as appropriate. For example, administration of the blocking agent(s) can be discontinued if the level of maternal antibodies falls below the predetermined threshold level. The blocking agent(s) can be administered for the full duration of a pregnancy, or during one or more of the first, second or third trimesters of pregnancy. Administration can begin before conception and can continue after birth, for example, while the mother is breast-feeding the child.

In some embodiments where the blocking agent(s) is a peptide or mimotope thereof, typical dosages can range from about 0.1 µg/kg body weight up to and including about 1 g/kg body weight, for example, between about 1 µg/kg body weight to about 500 mg/kg body weight. In some embodiments, the dose of peptide or mimotope is about 1, 2, 3, 4, 5, 10, 20, 30, 40, 50, 60, 70, 80, 90, or 100 mg/kg body weight.

The exact dose will depend on a variety of factors as described herein, including the particular inhibitor, severity of the disease, and route of administration. Determining the exact therapeutically effective dose can be determined by a clinician without undue experimentation and can include any dose included within the ranges disclosed above.

The blocking agent(s) are administered by a route of administration such that the agent(s) bind to the maternal antibodies and prevents the binding of the antibodies to endogenous autoantigens associated with risk of developing ASD and that immune responses to the agent are minimized. Usually the agent(s) are administered systemically. In some embodiments, the agent(s) are administered parenterally, e.g., intravenously or intra-amniotically (i.e., directly into the amniotic sac). Additionally, the agent(s) may be administered orally.

The blocking agent(s) can be formulated for parenteral administration by injection, e.g., by bolus injection or continuous infusion. For injection, blocking agent(s) can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some embodiments, a combination of blocking agents can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the blocking agent(s) in water-soluble form. Additionally, suspensions of the blocking agent(s) can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the blocking agent(s) can be in powder form for constitution with a suitable vehicle, e.g., sterile pyrogen-free water, before use.

Treatment with the blocking agent(s) is considered efficacious if the levels or titer of maternal antibodies that actively bind to one or more endogenous autoantigens are reduced or eliminated in a biological sample from an individual after receiving one or more administrations of the blocking agent(s), in comparison to before administration of the blocking agent(s). For example, a reduction of maternal antibodies that actively bind to one or more endogenous autoantigens in a sample of at least about 10%, 25%, 50%, 75% or 100% after one or more administrations of one or more blocking agents indicates that administration of the blocking agent(s) was efficacious. Where a threshold level has been established, treatment with the blocking agent(s) is considered efficacious if the levels or titer of maternal antibodies that actively bind to one or more endogenous autoantigens are reduced to below the threshold level. Maternal antibodies that actively bind to one or more endogenous autoantigens can be measured using any method known in the art, including those described herein.

G. Methods of Reducing Risk by Removing Maternal Antibodies

In certain aspects, the present invention provides methods of preventing or reducing a risk of an offspring such as a fetus or child for developing an autism spectrum disorder (ASD) by removing the maternal antibodies from a biological fluid of the mother or potential mother ex vivo, and then returning the biological fluid, with reduced or eliminated levels of maternal antibodies, to the mother or potential mother.

In some embodiments, biological fluid containing maternal antibodies can be removed from the mother or potential mother and contacted with one or more of the peptides described herein. In other embodiments, one or more of the peptides described herein can be administered to the mother or potential mother to block the binding between maternal autoantibodies and their autoantigens in a biological fluid, thereby neutralizing the maternal autoantibodies, and the neutralized complexes present in the biological fluid are removed using an extracorporeal therapy, such as affinity plasmapheresis.

In some embodiments, biological fluid from the mother or potential mother is contacted with one or more of the peptides immobilized on a solid support. The solid support can be, for example, a multiwell plate, an ELISA plate, a microarray, a chip, a bead, a column, a porous strip, a membrane, or a nitrocellulose filter. The immobilization can be via covalent or non-covalent binding. In some embodiments, the immobilization is through a capture antibody that specifically binds to the target peptide epitope. The peptide(s) attached to the solid support is a stationary phase that captures the maternal antibodies in the biological fluid, allowing the biological fluid with reduced or eliminated levels of maternal antibodies to be separated from the solid support, i.e., as the mobile phase, and returned to the mother or potential mother.

In some embodiments, the biological fluid that is processed ex vivo is plasma, and the maternal antibodies are removed by plasmapheresis, a process well known in the art. The plasma is contacted with a solid support with one or more immobilized peptides. Maternal antibodies in the plasma bind to the immobilized peptides. Plasma with reduced or eliminated levels of maternal antibodies is then returned to the mother or potential mother.

The ex vivo removal of maternal antibodies can be carried out on a woman before, during, or after pregnancy. In some embodiments, the maternal antibodies are removed from the biological fluid one, two, three, four or more times, as appropriate, at any time during the course of pregnancy. For example, the maternal antibodies can be removed in one or more of the first, second and/or third trimesters of pregnancy. In some embodiments, the maternal antibodies are removed from a woman carrying a fetus whose brain has begun to develop, e.g., after about 12 weeks of gestation. In some embodiments, the maternal antibodies are removed one or more times post-partum, e.g., in the first four weeks after birth and/or while the mother is breastfeeding the child. In some embodiments, the maternal antibodies are removed one or more times before pregnancy, for example, in a woman who has tested positive for maternal antibodies and who is trying to become pregnant.

The process of ex vivo maternal antibody removal can be performed one, two, three, four, or more times, as needed to eliminate or reduce maternal antibodies from the mother or potential mother. Ex vivo removal of the maternal antibodies can be performed daily, weekly, bi-weekly, monthly, bi-monthly, as appropriate. In some embodiments, the levels of maternal antibodies in the mother or potential mother are monitored and ex vivo maternal antibody removal performed if the presence of maternal antibodies are above a predetermined threshold level. Ex vivo maternal antibody removal can be carried out over a time period of a 1, 2, 3, 4, 5, 10, 12, 15, 20, 25, 35, 36 weeks, or longer or shorter, as appropriate. For example, ex vivo removal of maternal antibodies can be discontinued if the level of maternal antibodies falls below the predetermined threshold level. Ex vivo maternal antibody removal can be conducted for the full duration of a pregnancy, or during one or more of the first, second or third trimesters of pregnancy. Maternal antibody removal can begin before conception and can continue after birth, for example, while the mother is breast-feeding the child.

The biological fluid containing maternal antibodies is usually blood, serum, plasma, or milk. In some embodiments, the biological fluid is amniotic fluid.

IV. EXAMPLES

The following examples are offered to illustrate, but not to limit the claimed invention.

Example 1. Identification of Native Peptide Epitopes for Maternal Antibodies Associated with Autism Spectrum Disorders This example describes a study that was performed to determine the peptide sequences of autoantigens including lactate dehydrogenase A and B (LDH A and LDH B), stress-induced phosphoprotein 1 (STIP1), collapsin response mediator proteins 1 and 2 (CRMP1 and CRMP2), guanine deaminase (GDA) and Y-box binding protein (YBX1) that are targeted by autism-specific maternal antibodies.

Banked maternal plasma samples were provided by The Childhood Autism Risk from Genetics and Environment (CHARGE) Study at the University of California, Davis M.I.N.D. Institute. In this study, plasma was utilized from mothers who have children with autism spectrum disorders (ASD; n=55) and from mothers of typically developing children (TD; n=31), all of which have been characterized for their reactivity to fetal brain proteins. Diagnosis of all enrolled children was confirmed at the UC Davis M.I.N.D. Institute.

To delineate the specific antibody-binding peptide epitopes, an overlapping peptide-scanning methodology was utilized. The amino acid sequences for each of the candidate autoantigens was obtained from the NCBI protein database. Working in conjunction with PEPperPrint® (Heidelberg, Germany), each protein was translated into a peptide array composed of overlapping peptide sequences. Each peptide contained 15 amino acids with a 14 amino acid peptide-peptide overlap. In addition, each peptide was elongated with neutral GSGSGSG (SEQ ID NO: 120) linkers at the N- and C-termini to avoid truncated peptides and to ensure that peptides were separated from one another.

Two different discovery microarrays were synthesized for the experiments: one microarray (Scheme #1) contained Lactate Dehydrogenase A (LDH A, GenBank Accession AAH67223), Stress-Induced Phosphoprotein 1 (STIP1 GenBank Accession AAH39299), and Collapsin Response Mediator Protein 1 (CRMP1, GenBank Accession NP_001014809); and the other microarray (Scheme #2) contained Lactate Dehydrogenase B (LDH B, GenBank Accession CAA32033), Guanine Deaminase (GDA, Gen- Bank Accession AAH53584), Y-Box Binding Protein 1 (YBX1, GenBank Accession AA106046), and Collapsin Response Mediator Protein 2 (CRMP2, GenBank Accession NP_001184222). Microarray Scheme #1 contained 1,537 different peptides that were printed in duplicate (3,074 spots total) and Scheme #2 contained 1,810 different peptides that were printed in duplicate (3,620 spots total). FLAG (DYKDDDDKGG; SEQ ID NO:116) and HA (YPYDVPDYAG; SEQ ID NO:117) control peptides also framed each array. Three to six glass slides for each microarray were synthesized and each was incubated with a maternal plasma sample. The plasma samples were either predetermined via Western blotting to be reactive to all of the proteins of the microarray, or a combination of maternal plasma samples in which each sample was found to be highly reactive to at least one of the autoantigens.

Each microarray was treated as follows: Prior to incubating with the sample, the slide was incubated for pre-swelling in the standard buffer for 10 minutes and in the blocking buffer for 45 minutes at room temperature. The maternal plasma samples (diluted 1:250 in staining buffer) were incubated with the slides overnight at 4° C. with shaking. The microarrays were then incubated for 10 minutes in standard buffer, and then for 30 minutes at room temperature with the labeled antibodies, such as the HA and FLAG control antibodies (anti-HA-Cy5 and anti-FLAG-Cy5, respectively, diluted 1:1,000 in staining buffer) or the DyLight680 (Rockland #609-144-123) labeled secondary F(ab')2 goat anti-human IgG (H+L) antibody (diluted 1:5, 000 in staining buffer). Peptide microarray staining as described above was performed using a PEPperCHIP© staining kit. Rockland blocking buffer MB-070, Phosphate Buffered Saline with 0.05% Tween 20, and Phosphate Buffered Saline with 0.05% Tween 20 and 10% Rockland blocking buffer were used for blocking, washing, and staining, respectively.

The light emission from the microarrays was detected using a GenePix 4000B® Microarray Scanner. Quantification of spot intensities and peptide annotation was performed using PepSlide® Analyzer. This software provides an algorithm that breaks down the fluorescence intensities of each spot into raw, foreground, and background signals. The calculated median foreground intensities reflect the extent of antibody binding to the selected peptides. P-values were obtained using a two-tailed Fisher's Exact Test. A peptide was called as positive (reactive) for a given sample if both of the following criteria were met:

1. The Chebyshev inequality (CI) p-value, calculated based on the red raw mean data, was less than 0.05 for both spots for that peptide. The CI p-value was defined as $$CI - p - \text{Value} = \begin{cases} 1 & Y_k \leq \overline{X} + s \\ \left( \dfrac{s}{(Y_k - \overline{X})} \right)^2 & Y_k > \overline{X} + s \end{cases}$$

where $Y_k$ was the observed fluorescence for a spot, s was the sample standard deviation of control spots on the array and $\overline{X}$ was the sample mean of control spots on the array.

2. The coefficient of variation between duplicate spots was less than 50%.

The expected (control) spot pattern of the HA and FLAG control peptides framing the microarray was detected. Clearly detectable epitope-like spot patterns formed by rows of neighbored peptides was seen. Table 1 represents the antigenic peptides identified by the microarray studies. Table 2 represents the peptide epitopes for each target antigen after overlapping amino acid sequences were combined. For example, SEQ ID NO:62 in Table 2 is a peptide epitope that results from combining the overlapping sequences of SEQ ID NOS:2 and 3 set forth in Table 1.

TABLE 1

| Peptide Epitopes for Each Target Antigen | | |
|---|---|---|
| Antigen | SEQ ID NO | Amino acid sequence |
| LDH A | SEQ ID NO: 1 | DLADELALVDVIEDK |
| | SEQ ID NO: 2 | ADELALVDVIEDKLK |
| | SEQ ID NO: 3 | VDVIEDKLKGEMMDL |
| | SEQ ID NO: 4 | FLRTPKIVSGKDYNV |
| | SEQ ID NO: 5 | MKNLRRVHPVSTMIK |
| | SEQ ID NO: 6 | VHPVSTMIKGLYGIK |
| | SEQ ID NO: 7 | CHGWVLGEHGDSSVP |
| LDH B | SEQ ID NO: 8 | LIAPVAEEEATVPNN |
| | SEQ ID NO: 9 | PVAEEEATVPNNKIT |
| | SEQ ID NO: 10 | LQTPKIVADKDYSVT |
| | SEQ ID NO: 11 | TPKIVADKDYSVTAN |
| | SEQ ID NO: 12 | DCIIIVVSNPVDILT |
| | SEQ ID NO: 13 | CIIIVVSNPVDILTY |
| | SEQ ID NO: 14 | IIVVSNPVDILTYVT |
| | SEQ ID NO: 15 | VAGVSLQELNPEMGT |
| | SEQ ID NO: 16 | ESMLKNLSRIHPVST |
| | SEQ ID NO: 17 | MLKNLSRIHPVSTMV |
| | SEQ ID NO: 18 | VSTMVKGMYGIENEV |
| | SEQ ID NO: 19 | VFLSLPCILNARGLT |
| STIP1 | SEQ ID NO: 20 | VLLGVDLGSMDEEEE |
| | SEQ ID NO: 21 | VDLGSMDEEEEIATP |
| | SEQ ID NO: 22 | PPPPPPKKETKPEPM |
| | SEQ ID NO: 23 | TNQAAVYFEKGDYNK |
| GDA | SEQ ID NO: 24 | PPLAHIFRGTFVHST |
| | SEQ ID NO: 25 | SSIDLPLLEWLTKYT |
| | SEQ ID NO: 26 | ATIHTDSSLLLADIT |
| | SEQ ID NO: 27 | MDLNDTFPEYKETTE |
| YBX1 | SEQ ID NO: 28 | PAAPPAAPALSAADT |
| | SEQ ID NO: 29 | ATKVLGTVKWFNVRN |
| | SEQ ID NO: 30 | TVKWFNVRNGYGFIN |
| | SEQ ID NO: 31 | FNVRNGYGFINRNDT |
| | SEQ ID NO: 32 | ETVEFDVVEGEKGAE |
| | SEQ ID NO: 33 | GAEAANVTGPGGVPV |
| | SEQ ID NO: 34 | RRPYRRRRFPPYYMR |
| | SEQ ID NO: 35 | PPRQRQPREDGNEED |
| CRWIP1 | SEQ ID NO: 36 | VVPEPGSSLLTSFEK |
| | SEQ ID NO: 37 | TSFEKWHEAADTKSC |
| | SEQ ID NO: 38 | VDITSWYDGVREELE |
| | SEQ ID NO: 39 | VTSPPLSPDPTTPDY |
| | SEQ ID NO: 40 | MDENQFVAVTSTNAA |
| | SEQ ID NO: 41 | VGSDADVVIWDPDKL |
| | SEQ ID NO: 42 | VYEVPATPKYATPAP |
| | SEQ ID NO: 43 | VPATPKYATPAPSAK |
| | SEQ ID NO: 44 | QSNFSLSGAQIDDNN |
| CRMP2 | SEQ ID NO: 45 | MAERKQSGKAAEDEE |
| | SEQ ID NO: 46 | VNDDQSFYADIYMED |
| | SEQ ID NO: 47 | GENLIVPGGVKTIEA |
| | SEQ ID NO: 48 | VVPEPGTSLLAAFDQ |
| | SEQ ID NO: 49 | VPEPGTSLLAAFDQW |
| | SEQ ID NO: 50 | QKAVGKDNFTLIPEG |
| | SEQ ID NO: 51 | TSPPLSPDPTTPDFL |
| | SEQ ID NO: 52 | VGSDADLVIWDPDSV |
| | SEQ ID NO: 53 | VKTISAKTHNSSLEY |
| | SEQ ID NO: 54 | KTISAKTHNSSLEYN |
| | SEQ ID NO: 55 | HNSSLEYNIFEGMEC |
| | SEQ ID NO: 56 | ELRGVPRGLYDGPVC |
| | SEQ ID NO: 57 | LRGVPRGLYDGPVCE |
| | SEQ ID NO: 58 | RGVPRGLYDGPVCEV |
| | SEQ ID NO: 59 | GVPRGLYDGPVCEVS |
| | SEQ ID NO: 60 | VPRGLYDGPVCEVSV |
| | SEQ ID NO: 61 | SLSGAQIDDNIPRRT |

TABLE 2

Combined Peptide Epitopes for Each Target Antigen

| Antigen | SEQ ID NO | Amino acid sequence |
|---|---|---|
| LDH A | SEQ ID NO: 62 | ADELALVDVIEDKLKGEMMDL |
| | SEQ ID NO: 63 | FLRTPKIVSGKDYNV |
| | SEQ ID NO: 64 | MKNLRRVHPVSTMIKGLYGIK |
| | | |
| LDH B | SEQ ID NO: 65 | EKLIAPVAEEEATVPNNKIT |
| | SEQ ID NO: 66 | IAPVAEEEATVPNNKIT |
| | SEQ ID NO: 67 | DCIIIVVSNPVDILTYVT |
| | SEQ ID NO: 68 | VAGVSLQELNPEMGT |
| | SEQ ID NO: 69 | NEVFLSLPCILNARGLT |
| | SEQ ID NO: 70 | FLQTPKIVADKDYSVTAN |
| | SEQ ID NO: 71 | LQTPKIVADKDYSVTAN |
| | SEQ ID NO: 72 | ESMLKNLSRIHPVSTMVKGMYGIEV |
| | | |
| STIP1 | SEQ ID NO: 73 | VLLGVDLGSMDEEEEIAT |
| | SEQ ID NO: 74 | PPPPPPPKKETKPEPME |
| | SEQ ID NO: 75 | PPPPPPKKETKPEPME |
| | SEQ ID NO: 76 | TNQAAVYFEKGDYNK |
| | | |
| GDA | SEQ ID NO: 77 | PPLAHIFRGTFVHST |
| | SEQ ID NO: 78 | SSIDLPLLEWLTKYT |
| | SEQ ID NO: 79 | ATIHTDSSLLLADIT |
| | | |
| YBX1 | SEQ ID NO: 80 | ATKVLGTVKWFNVRNGYGFINRNDT |
| | SEQ ID NO: 81 | ETVEFDVVEGEKGAEAANVTGPGGVPV |
| | SEQ ID NO: 82 | RRPYRRRRFPPYYMR |
| | SEQ ID NO: 83 | PPRQRQPREDGNEED |
| | | |
| CRMP1 | SEQ ID NO: 84 | SFEKWHEAADTKSC |
| | SEQ ID NO: 85 | MDENQFVAVTSTNAA |
| | SEQ ID NO: 86 | VPATPKYATPAPSAK |
| | SEQ ID NO: 87 | VTSPPLSPDPTTPDYL |
| | SEQ ID NO: 88 | QSNFSLSGAQIDDNN |
| | | |
| CRMP2 | SEQ ID NO: 89 | VNDDQSFYADIYMED |
| | SEQ ID NO: 90 | GENLIVPGGVKTIEA |
| | SEQ ID NO: 91 | QKAVGKDNFTLIPEG |
| | SEQ ID NO: 92 | VKTISAKTHNSSLEYNIFEGMEC |
| | SEQ ID NO: 93 | ELRGVPRGLYDGPVCEVSV |
| | SEQ ID NO: 94 | VVPEPGTSLLAAFDQW |
| | SEQ ID NO: 95 | TSPPLSPDPTTPDFL |
| | SEQ ID NO: 96 | SLSGAQIDDNIPRRT |

Example 2. Differentiating Samples Obtained from Mothers with Children Diagnosed with Autism Spectrum Disorder from Samples Obtained from Mothers with Typically Developing Children This example describes a study that demonstrated that the peptides of the present invention are useful for differentiating plasma samples obtained from mothers who have children with an autism spectrum disorder (ASD) from those obtained from mothers who have typically developing (TD) children. In particular, this example illustrates that the peptides of the present invention can be used to determine a risk of a child for developing an ASD by detecting in a sample from the mother (or potential mother) of the child the presence of autoantibodies that bind to one or more (e.g., a plurality) of the peptides.

For these experiments, identical validation microarrays were constructed, each containing the peptides listed in Tables 1 and 2. Each microarray also contained several peptides that were not bound by any maternal plasma samples during the experiments described in Example 1 as negative controls. In addition, a peptide derived from poliovirus (KEVPALTAVETGAT; SEQ ID NO:118) was used as a positive control. Each identical microarray contained the peptides in duplicate in a random distribution and was framed by FLAG (DYKDDDDKGG; SEQ ID NO:116) and HA (YPYDVPDYAG; SEQ ID NO:117) control peptides.

The validation microarrays were treated and processed as described in Example 1. Validation microarrays were incubated with maternal plasma samples that were pre-determined via western blot and ELISA to be highly reactive to at least one of the candidate autoantigens. Light emission from the microarrays was measured and analyzed as described in Example 1.

Table 3 shows that some of the peptides in Tables 1 and 2 are useful for distinguishing samples obtained from mothers who have children diagnosed with ASD from samples obtained from mothers who have TD children. Peptides denoted by SEQ ID NOS: 9, 11, 12, 36, 54, 66, and 71 were only bound by autoantibodies when the microarrays were incubated with plasma samples obtained from mothers whose children had a diagnosis of ASD (i.e., no peptides were bound by antibodies when microarrays were incubated with samples obtained from mothers of TD children). Other peptides were more often bound by autoantibodies when the microarrays were incubated with plasma samples from mothers whose children had a diagnosis of ASD, compared to when the microarrays were incubated with samples obtained from mothers of TD children.

In addition, Table 4 shows that combinations of the peptides listed in Table 3 may be used for distinguishing samples obtained from mothers of ASD children from samples obtained from mothers of TD children. Particular combinations of one or more, three or more, four or more, or five or more peptides, when used for the analysis, were able to distinguish samples obtained from mothers of ASD children from samples obtained from mothers of TD children with statistical significance. Table 5 lists some examples of the combinations of peptides from Table 1 in which binding of autoantibodies was detected in samples obtained from mothers of ASD children, but not in samples obtained from mothers of TD children. In some instances, all peptides in a given combination were derived from the same autoantigen. In other instances, peptides from two, three, or four different autoantigens were used.

These results also indicate that the peptides are useful for detecting antibodies that bind to different regions of the same autoantigen. These peptides provide additional information in situations where samples either do not show antibody binding to the corresponding full-length autoantigens themselves, or where a test sample and a control sample (e.g., a plasma sample from a mother with a TD child) both exhibit antibody binding to a particular autoantigen.

TABLE 3

Utilizing Maternal Autoantibody Reactivity to Differentiate ASD from TD

| SEQ ID NO | Amino acid sequence | Antigen | Number Positive In ASD (n = 46) | Number (%) Positive In ASD | Number Positive In TD (n = 21) | Number (%) Positive In TD |
|---|---|---|---|---|---|---|
| SEQ ID NO: 3 | VDVIEDKLKGEMMDL | LDH A | 7 | 15% | 2 | 10% |
| SEQ ID NO: 12 | DCIIIVVSNPVDILT | LDH B | 5 | 11% | 0 | 0% |

TABLE 3-continued

| | | | | Number | Number | Number | |
| SEQ ID NO | | Amino acid sequence | Antigen | Positive In ASD (n = 46) | (%) Positive In ASD | Positive In TD (n = 21) | Number (%) Positive In TD |
|---|---|---|---|---|---|---|---|
| SEQ ID NO: | 9 | PVAEEEATVPNNKIT | LDH B | 3 | 7% | 0 | 0% |
| SEQ ID NO: | 66 | IAPVAEEEATVPNNKIT | LDH B | 2 | 4% | 0 | 0% |
| SEQ ID NO: | 71 | LQTPKIVADKDYSVTAN | LDH B | 1 | 2% | 0 | 0% |
| SEQ ID NO: | 11 | TPKIVADKDYSVTAN | LDH B | 1 | 2% | 0 | 0% |
| SEQ ID NO: | 32 | ETVEFDVVEGEKGAE | YBX1 | 5 | 11% | 1 | 5% |
| SEQ ID NO: | 28 | PAAPPAAPALSAADT | YBX1 | 19 | 41% | 6 | 29% |
| SEQ ID NO: | 27 | MDLNDTFPEYKETTE | GDA | 8 | 17% | 1 | 5% |
| SEQ ID NO: | 21 | VDLGSMDEEEEIATP | STIP1 | 6 | 13% | 1 | 5% |
| SEQ ID NO: | 20 | VLLGVDLGSMDEEEE | STIP1 | 14 | 30% | 4 | 19% |
| SEQ ID NO: | 38 | VDITSWYDGVREELE | CRMP1 | 12 | 26% | 3 | 14% |
| SEQ ID NO: | 36 | VVPEPGSSLLTSFEK | CRMP1 | 2 | 4% | 0 | 0% |
| SEQ ID NO: | 55 | HNSSLEYNIFEGMEC | CRMP2 | 16 | 35% | 4 | 19% |
| SEQ ID NO: | 54 | KTISAKTHNSSLEYN | CRMP2 | 1 | 2% | 0 | 0% |
| SEQ ID NO: | 45 | MAERKQSGKAAEDEE | CRMP2 | 10 | 22% | 1 | 5% |
| SEQ ID NO: | 60 | VPRGLYDGPVCEVSV | CRMP2 | 8 | 17% | 1 | 5% |

TABLE 4

Combinations of Peptides Bound by Maternal
Autoantibodies from the Plasma of
Mothers of Children with ASD and TD children

| Number of Peptides Bound by Maternal Autoantibodies | ASD (%) (n = 46) | TD (%) (n = 21) |
|---|---|---|
| ≥1 | 41 (89%) | 13 (62%) |
| ≥2 | 28 (61%) | 9 (43%) |
| ≥3 | 23 (50%) | 2 (10%) |
| ≥4 | 14 (30%) | 0 (0%) |
| ≥5 | 8 (18%) | 0 (0%) |

TABLE 4-continued

Combinations of Peptides Bound by Maternal
Autoantibodies from the Plasma of
Mothers of Children with ASD and TD children

| Number of Peptides Bound by Maternal Autoantibodies | ASD (%) (n = 46) | TD (%) (n = 21) |
|---|---|---|
| ≥6 | 3 (7%) | 0 (0%) |
| ≥7 | 2 (4%) | 0 (0%) |
| ≥8 | 1 (2%) | 0 (0%) |

TABLE 5

Specific Peptide Combinations for Differentiating ASD from TD Samples

| Combination | SEQ ID NO | | Amino acid sequence | Antigen | ASD | TD |
|---|---|---|---|---|---|---|
| 1 | SEQ ID NO: | 21 | VDLGSMDEEEEIATP | STIP1 | 4 | 0 |
| | SEQ ID NO: | 20 | VLLGVDLGSMDEEEE | STIP1 | | |
| 2 | SEQ ID NO: | 55 | HNSSLEYNIFEGMEC | CRMP2 | 4 | 0 |
| | SEQ ID NO: | 27 | MDLNDTFPEYKETIE | GDA | | |
| 3 | SEQ ID NO: | 55 | HNSSLEYNIFEGMEC | CRMP2 | 4 | 0 |
| | SEQ ID NO: | 20 | VLLGVDLGSMDEEEE | STIP1 | | |
| 4 | SEQ ID NO: | 55 | HNSSLEYNIFEGMEC | CRMP2 | 2 | 0 |
| | SEQ ID NO: | 45 | MAERKQSGKAAEDEE | CRMP2 | | |
| 5 | SEQ ID NO: | 9 | PVAEEEATVPNNKIT | LDH B | 2 | 0 |
| | SEQ ID NO: | 28 | PAAPPAAPALSAADT | YBX1 | | |
| 6 | SEQ ID NO: | 32 | ETVEFDVVEGEKGAE | YBX1 | 2 | 0 |
| | SEQ ID NO: | 20 | VLLGVDLGSMDEEEE | STIP1 | | |

TABLE 5-continued

Specific Peptide Combinations for Differentiating ASD from TD Samples

| Combination | SEQ ID NO | | Amino acid sequence | Antigen | ASD | TD |
|---|---|---|---|---|---|---|
| 7 | SEQ ID NO: | 45 | MAERKQSGKAAEDEE | CRMP2 | | |
| | SEQ ID NO: | 38 | VDITSWYDGVREELE | CRMP1 | 2 | 0 |
| | SEQ ID NO: | 27 | MDLNDTFPEYKETIE | GDA | | |
| 8 | SEQ ID NO: | 38 | VDITSWYDGVREELE | CRMP1 | | |
| | SEQ ID NO: | 55 | HNSSLEYNIFEGMEC | CRMP2 | 2 | 0 |
| | SEQ ID NO: | 21 | VDLGSMDEEEEIATP | STIP1 | | |
| 9 | SEQ ID NO: | 3 | VDVIEDKLKGEMMDL | LDH A | | |
| | SEQ ID NO: | 12 | DCIIIVVSNPVDILT | LDH B | 3 | 0 |
| | SEQ ID NO: | 27 | MDLNDTFPEYKETIE | GDA | | |
| | SEQ ID NO: | 28 | PAAPPAAPALSAADT | YBX1 | | |
| 10 | SEQ ID NO: | 32 | ETVEFDVVEGEKGAE | YBX1 | | |
| | SEQ ID NO: | 38 | VDITSWYDGVREELE | CRMP1 | | |
| | SEQ ID NO: | 55 | HNSSLEYNIFEGMEC | CRMP2 | 2 | 0 |
| | SEQ ID NO: | 45 | MAERKQSGKAAEDEE | CRMP2 | | |
| | SEQ ID NO: | 60 | VPRGLYDGPVCEVSV | CRMP2 | | |

Example 3. ELISA-Based Assays for Detecting Antibodies in a Maternal Sample that Specifically Bind to Antigenic Peptides This example describes a method of making an ELISA-based assay for the detection of maternal antibodies that bind to an antigenic peptide. The presence of the maternal antibody in a mother or potential mother is associated with a risk of having a child with an autism spectrum disorder. This example also illustrates the use of the ELISA-based assay to identify at-risk mothers or potential mothers.

The peptides of Table 2 were synthesized with a linker and biotinylated. In particular, each biotinylated peptide was biotin-SGSS-peptide-DKP with SGSS (SEQ ID NO: 121) as the spacer and a diketopiperazine (DKP) group at the C-terminus of the peptide. Pierce® NeutrAvidin® protein coated microwell plates (Thermo Scientific) were washed with PBST and excess buffer was removed from the wells. The biotinylated peptides were reconstituted in pure solvent (e.g., DMSO or DMF) or a solvent/water mixture. The reconstituted peptide was diluted 1:250 in ultra pure water to a final concentration of 5 μg/ml. 100 μl of the diluted biotinylated peptide was dispensed into the wells and incubated for 1 hour at room temperature or overnight at 4° C. on a slow rocker. Reference wells were left uncoated but filled with buffer. Nonspecific binding sites were blocked by incubation with 200 μl of a 5% Pierce® Superblock™ PBS solution for 2 hours at room temperature. Subsequently, the plates were washed six times with PBST using an automated plate washer.

The following method adapted from Sanchez et al. (Cancer Chemother. Pharmacol., 66: 919-925 (2010)) was used to detect maternal antibodies against one or more of the peptides of the ELISA-based assay described above: Maternal plasma samples were obtained including samples predetermined to be reactive to the full-length antigens of the peptides in the assay. The test samples were diluted in sample diluent (e.g., 2.5% Pierce® Superblock™ in PBST) and 100 μl of each sample was added to the wells of the assay plate. All samples were analyzed in duplicate in both peptide-coated and uncoated wells. The diluted samples were incubated for 1 hour at room temperature. The plates were then washed six times with PBST. The labeled secondary antibody solution (e.g., horseradish peroxidase-conjugated goat anti-human IgG, Invitrogen) was added to the wells and incubated for 30 minutes at room temperature. The plates were again washed eight times with PBST. The plates were then washed with PBS without Tween twice. The BD Opt EIA™ substrate (BD Biosciences Pharmingen, San Diego, CA) was added to the wells and incubated at room temperature for 10 minutes. The STOP solution (2N H2504) was added and the plate was read at 450 nm using a reference filter at 490 nm.

Example 4. Determination of Reactivity of Maternal Samples to a STIP1 Peptide

This example illustrates that maternal plasma samples exhibited a higher reactivity to a STIP1 peptide of the present invention when compared to the full-length STIP1 polypeptide. In particular, four maternal plasma samples were tested for their reactivity to a STIP1 peptide having the amino acid sequence PPPPPPKKETKPEPM (SEQ ID NO:22) using the following peptide ELISA protocol:

1. Bring all reagents to room temperature.
2. Peptides were diluted in ultra pure water from peptide stock (1 mg/mL) to a final concentration of 5 μg/mL.
3. Add 100 μl of each peptide to corresponding wells on 96-well NeutrAvidin coated plate.
4. Incubate plate for 1 hour at room temperature.
5. Wash plate six times with PBS with 0.05% Tween.
6. Add 200 μl of 5% Superblock to each well and incubated for 2 hours at room temperature.
7. Wash plate six times with PBS with 0.05% Tween.
8. Dilute maternal plasma samples 1:400 in sample buffer (2.5% Superblock in PBS with 0.05% Tween).
9. Add 100 μl of diluted plasma samples to wells and incubate for 1 hour at room temperature.
10. Wash plate six times with PBS with 0.05% Tween.
11. Dilute Goat Anti-Human antibody 1: 2,500 in PBS with 0.05% Tween.
12. Add 100 μl of diluted Goat Anti-Human antibody to wells and incubate for 30 minutes at room temperature.
13. Wash plate eight times with PBS with 0.05% Tween and two times with PBS Neat.
14. Add 100 μl of BD Opt EIA substrate to each well.
15. Incubate plate in the dark for 10 minutes at room temperature.

16. Add 50 µl of H2504 to each well to stop chemical reaction.

17. Read plate on reduced setting on spectrophotometer at 450 nm with 490 nm reference.

The samples were run in duplicate and the absorbance values were averaged. Table 6 shows that Sample No. 1190 was especially reactive to the STIP1 peptide (Final absorbance=2.045). In contrast, the absorbance value obtained for the same sample using an ELISA with the full-length STIP1 polypeptide was near 1.0. As such, this example demonstrates that the peptides of the present invention display high reactivity to autoantibodies present in a maternal sample and provide improved sensitivity over the full-length polypeptide sequence.

TABLE 6

STIP1 Peptide ELISA Data

| Sample No. 99 (Medium Reactivity) | |
| --- | --- |
| Average | 1.482 |
| SD | 0.042 |
| % CV | 2.816 |
| Blank | 0.999 |
| Final | 0.483 |
| Sample No. 142 (Negative) | |
| Average | 1.295 |
| SD | 0.004 |
| % CV | 0.328 |
| Blank | 1.202 |
| Final | 0.093 |
| Sample No. 1190 (Highly Reactive) | |
| Average | 2.442 |
| SD | 0.103 |
| % CV | 4.199 |
| Blank | 0.397 |
| Final | 2.045 |
| Sample No. 1887 (Low Reactivity) | |
| Average | 2.101 |
| SD | 0.110 |
| % CV | 5.218 |
| Blank | 1.972 |
| Final | 0.129 |

Example 5. Mouse Model for Maternal Antibody Related Autism Spectrum Disorders This example illustrates the creation and characterization of a mouse model for maternal antibody related autism spectrum disorders (MAR-ASD) that can be used to examine the efficacy, safety, and/or pharmacokinetic properties of the peptides of the present invention or mimotopes thereof in vivo. MAR-ASD mice were created by immunizing adult female mice with peptides from lactate dehydrogenase A (LDH-A), lactate dehydrogenase B (LDH-B), collapsin response mediator protein 1 (CRMP1), and stress-induced phosphoprotein 1 (STIP1) that were conjugated to a branched backbone in which lysine residues were used as the scaffolding core. Animals received a total of five immunizations prior to breeding. At each immunization, animals were injected with 100 µL of a peptide-adjuvant-saline mix. With the exception of the fourth immunization, for each immunization 8.4 µg each of LDH A, LDH B, and CRMP petpides, together with 16.4 µg of STIP1 peptides, were administered at the same time. The fourth immunization contained 25 µg of STIP1 peptides and 15 µg of whle STIP1 protein, in addition to adjuvant. Control animals received a similar number of injections containing 100 µL of saline only. Tolerance to individual MAR-ASD peptide epitopes was successfully broken in the females prior to breeding, as evidenced by ELISA assay. Optical density measurements that were made to assay immunoreactivity of all peptides were significantly higher (approximately four-fold), in MAR-ASD animals than control animals (p<0.001).

Developmental milestones were examined in offspring of MAR-ASD mice and compared to the offspring of controls. Body weight and head width were measured in 22 MAR-ASD offspring and 17 control offspring. Offspring that were exposed to autism-specific maternal antibodies were significantly larger in body weight at postnatal days 4, 6, 8, 10, 12, and 14 (p=0.009). In addition, head width in MAR-ASD offspring was significantly larger than controls at postnatal days 12 and 14 (p<0.001). The observed increases in head width remained significant when adjusted for total body length, indicating that the differences in head size were independent of total body size.

MAR-ASD offspring also displayed several behavioral abnormalities relevant to autism, including alterations in neurodevelopment, increased repetitive self-grooming behaviors, diminished ultrasonic vocalizations, and deficits in social interactions. Juvenile reciprocal social interactions (JRSI) as well as male-female social interactions (MFSI) were assessed.

To assess JRSI, MAR-ASD offspring were examined for several behaviors on postnatal day 25, during ten-minute play sessions with age- and sex-matched novel C57BL/6J strangers. Behaviors in 24 MAR-ASD offspring were compared to 22 controls. MAR-ASD offspring displayed significant deficits in a number of behaviors, including decreased nose-to-nose (p=0.021) and anogenital sniffing (p=0.029), decreased push-crawl (p<0.001), front approach (p<0.001) and following behaviors (p=0.043), and increased self-grooming (approximately 3-fold; p<0.001).

MFSI was examined during five-minute play sessions in which adult male offspring were placed with unfamiliar age-matched females in estrus (MAR-ASD, n=12; control, n=11). MAR-ASD offspring displayed significant deficits in a number of behaviors when compared to controls, including decreased nose-to-anogenital (p=0.044) and body sniffing (p=0.041), decreased front approach (p=0.017) and following behaviors (p<0.001), and increased self-grooming (p=0.005).

In addition to the above developmental abnormalities, offspring that were exposed to autism-specific maternal antibodies exhibited several neuroanatomical differences, when compared to controls, in their adult brains, as assessed by MRI. Female MAR-ASD brains were significantly larger in total brain volume compared to male MAR-ASD brains and male and female control brains. Increases in size of several cortical regions (mainly in the orbital and visual cortices) and white matter tracts (including the anterior commissure, cingulum, corpus callosum, and internal capsule) were observed in MAR-ASD adult brains relative to controls, with observed differences primarily driven by the MAR-ASD females.

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and sequence accession numbers cited herein are hereby incorporated by reference in their entirety for all purposes.

What is claimed is:

1. A method of detecting an anti-collapsin response mediator protein 1 (CRMP1) antibody in a mother or potential mother comprising:

detecting whether the anti-CRMP1 antibody is present in a blood, serum, or plasma sample from the mother or potential mother by contacting the sample with (i) an isolated peptide consisting of 12 to 15 contiguous amino acids of the amino acid sequence of SEQ ID NO: 36 or 38, or (ii) an isolated peptide consisting of 12 to 15 contiguous amino acids of an amino acid sequence having at least 80% sequence identity to the amino acid sequence of SEQ ID NO: 36 or 38; and determining that the anti-CRMP1 antibody is present in the mother or potential mother after detecting binding between the anti-CRMP1 antibody in the sample and the isolated peptide.

2. The method of claim 1, wherein the peptide consists of 13, 14, or 15 contiguous amino acids of SEQ ID NO: 36.

3. The method of claim 1, wherein the peptide consists of 13, 14, or 15 contiguous amino acids of SEQ ID NO: 38.

4. The method of claim 1, wherein the peptide is a mimotope comprising D-amino acids.

5. The method of claim 4, wherein the mimotope comprises all D-amino acids.

6. The method of claim 1, wherein the peptide comprises a label.

7. The method of claim 6, wherein the label is selected from the group consisting of biotin, a fluorescent label, a chemiluminescent label, and a radioactive label.

8. The method of claim 1, wherein the peptide is attached to a solid support.

9. The method of claim 8, wherein the solid support is a multiwell plate, an ELISA plate, a microarray, a chip, a bead, a porous strip, or a nitrocellulose filter.

10. The method of claim 1, wherein the anti-CRMP1 antibody is detected by Western blot, dot blot, ELISA, radioimmunoassay, immunoprecipitation, electrochemiluminescence, immunofluorescence, FACS analysis, or multiplex bead assay.

11. The method of claim 1, wherein the mother or potential mother has a child with an ASD.

12. The method of claim 1, wherein the mother or potential mother has a familial history of ASD or autoimmune disease.

13. A method of diagnosing and treating a mother or potential mother having an increased risk of having offspring at risk for developing an autism spectrum disorder (ASD) comprising:

contacting a biological sample of the mother or potential mother of the offspring with (i) an isolated peptide consisting of 12 to 15 contiguous amino acids of the amino acid sequence of SEQ ID NO: 36 or 38, or (ii) an isolated peptide consisting of 12 to 15 contiguous amino acids of an amino acid sequence having at least 80% sequence identity to the amino acid sequence of SEQ ID NO: 36 or 38;

detecting the presence or absence of maternal antibodies that bind to the peptide in the biological sample, wherein the biological sample is selected from the group consisting of blood, serum, and plasma, and wherein the presence of maternal antibodies that bind to the peptide indicates an increased risk of the mother or potential mother for having offspring at risk for developing an ASD;

removing plasma from the mother or potential mother by plasmapheresis;

contacting the plasma removed from the mother or potential mother with (i) the isolated peptide consisting of 12 to 15 contiguous amino acids of the amino acid sequence of SEQ ID NO: 36 or 38, or (ii) the isolated peptide consisting of 12 to 15 contiguous amino acids of an amino acid sequence having at least 80% sequence identity to the amino acid sequence of SEQ ID NO: 36 or 38, wherein the isolated peptide is on a solid support to bind antibodies in the plasma that bind to the peptide; and returning the contacted plasma to the mother or potential mother to reduce the increased risk of having offspring at risk for developing an ASD.

14. The method of claim 13, wherein the peptide consists of 13, 14, or 15 contiguous amino acids of SEQ ID NO: 36.

15. The method of claim 13, wherein the peptide consists of 13, 14, or 15 contiguous amino acids of SEQ ID NO: 38.

16. The method of claim 13, wherein the peptide is a mimotope comprising D-amino acids.

17. The method of claim 16, wherein the mimotope comprises all D-amino acids.

18. The method of claim 13, wherein the peptide comprises a label.

19. The method of claim 18, wherein the label is selected from the group consisting of biotin, a fluorescent label, a chemiluminescent label, and a radioactive label.

20. The method of claim 13, wherein the peptide is attached to a solid support.

21. The method of claim 20, wherein the solid support is a multiwell plate, an ELISA plate, a microarray, a chip, a bead, a porous strip, or a nitrocellulose filter.

22. The method of claim 13, wherein the maternal antibodies are detected by Western blot, dot blot, ELISA, radioimmunoassay, immunoprecipitation, electrochemiluminescence, immunofluorescence, FACS analysis, or multiplex bead assay.

23. The method of claim 13, wherein the mother or potential mother has a child with an ASD.

24. The method of claim 13, wherein the mother or potential mother has a familial history of ASD or autoimmune disease.

25. The method of claim 13, wherein the method further comprises contacting the biological sample with a peptide having an amino acid sequence selected from the group consisting of SEQ ID NOS: 12, 21, 27 and 55; and detecting the presence of a maternal antibody to the peptide.

26. A method of detecting an anti-collapsin response mediator protein 1 (CRMP1) antibody in a mother or potential mother comprising:

detecting whether the anti-CRMP1 antibody is present in a blood, serum, or plasma sample from the mother or potential mother by contacting the sample with (i) an isolated peptide comprising the amino acid sequence of SEQ ID NO: 36 or 38, or (ii) an isolated peptide comprising an amino acid sequence having at least 80% sequence identity to the amino acid sequence of SEQ ID NO: 36 or 38;

and determining that the anti-CRMP1 antibody is present in the mother or potential mother after detecting binding between the anti-CRMP1 antibody in the sample and the isolated peptide.

27. A method of diagnosing and treating a mother or potential mother having an increased risk of having off-spring at risk for developing an autism spectrum disorder (ASD) comprising:

contacting a biological sample of the mother or potential mother of the offspring with (i) an isolated peptide comprising the amino acid sequence of SEQ ID NO: 36 or 38, or (ii) an isolated peptide comprising an amino acid sequence having at least 80% sequence identity to the amino acid sequence of SEQ ID NO: 36 or 38;

detecting the presence or absence of maternal antibodies that bind to the peptide in the biological sample, wherein the biological sample is selected from the group consisting of blood, serum, and plasma, and wherein the presence of maternal antibodies that bind to the peptide indicates an increased risk of the mother or potential mother for having offspring at risk for developing an ASD;

removing plasma from the mother or potential mother by plasmapheresis;

contacting the plasma removed from the mother or potential mother with (i) the isolated peptide comprising the amino acid sequence of SEQ ID NO: 36 or 38, or (ii) the isolated peptide comprising an amino acid sequence having at least 80% sequence identity to the amino acid sequence of SEQ ID NO: 36 or 38, wherein the isolated peptide is on a solid support to bind antibodies in the plasma that bind to the peptide; and returning the contacted plasma to the mother or potential mother to reduce the increased risk of having offspring at risk for developing an ASD.

* * * * *